US012232923B2

(12) United States Patent
Anssari Moin et al.

(10) Patent No.: US 12,232,923 B2
(45) Date of Patent: Feb. 25, 2025

(54) AUTOMATED ORTHODONTIC TREATMENT PLANNING USING DEEP LEARNING

(71) Applicant: Promaton Holding B.V., Amsterdam (NL)

(72) Inventors: David Anssari Moin, The Hague (NL); Frank Theodorus Catharina Claessen, The Hague (NL)

(73) Assignee: PROMATON HOLDING B.V., Amsterdam (NL)

( * ) Notice: Subject to any disclaimer, the term of this patent is extended or adjusted under 35 U.S.C. 154(b) by 535 days.

(21) Appl. No.: 17/272,460

(22) PCT Filed: Sep. 3, 2019

(86) PCT No.: PCT/EP2019/073438
§ 371 (c)(1),
(2) Date: Mar. 1, 2021

(87) PCT Pub. No.: WO2020/048960
PCT Pub. Date: Mar. 12, 2020

(65) Prior Publication Data
US 2021/0322136 A1   Oct. 21, 2021

(30) Foreign Application Priority Data
Sep. 4, 2018   (EP) .................................... 18192483

(51) Int. Cl.
*A61C 7/00*   (2006.01)
*A61C 7/08*   (2006.01)
(Continued)

(52) U.S. Cl.
CPC ................ *A61C 7/002* (2013.01); *A61C 7/08* (2013.01); *A61C 9/0053* (2013.01); *G06N 3/082* (2013.01);
(Continued)

(58) Field of Classification Search
CPC ......... A61C 7/002; A61C 7/08; A61C 9/0053; A61C 9/004; A61C 2007/004; A61C 7/00;
(Continued)

(56) References Cited

U.S. PATENT DOCUMENTS 6,721,387 B1   4/2004   Naidu et al.
7,987,099 B2   7/2011   Kuo et al.
(Continued)

FOREIGN PATENT DOCUMENTS

CN   101977564 A   2/2011
CN   106618760 A   5/2017
(Continued)

OTHER PUBLICATIONS

Gutierrez-Becker et al. "Learning Optimization Updates for Multimodal Registration", Medical Image Computing and Computer-Assisted Intervention—MICCAI 2016, 2016, pp. 19-27.
(Continued)

*Primary Examiner* — Nimesh Patel
(74) *Attorney, Agent, or Firm* — Steven M. Koehler; Westman, Champlin & Koehler, P.A.

(57) ABSTRACT

A method of the invention comprises obtaining training dental CT scans, identifying individual teeth and jaw bone in each of these CT scans, and training a deep neural network with training input data obtained from these CT scans and training target data. A further method of the invention comprises obtaining a patient dental CT scan, identifying individual teeth and jaw bone in this CT scan and using the trained deep learning network to determine a desired final position from input data obtained from this CT scan. The (training) input data represents all teeth and the entire alveolar process and identifies the individual teeth and the jaw bone. The determined desired final positions are used to
(Continued)

determine a sequence of desired intermediate positions per tooth and the intermediate and final positions and attachment types are used to create three-dimensional representations of teeth and/or aligners.

20 Claims, 20 Drawing Sheets

(51) Int. Cl.

| | | |
|---|---|---|
| A61C 9/00 | (2006.01) | |
| G06N 3/082 | (2023.01) | |
| G06T 7/00 | (2017.01) | |
| G06T 7/168 | (2017.01) | |
| G06V 10/44 | (2022.01) | |
| G06V 10/764 | (2022.01) | |
| G06V 10/82 | (2022.01) | |
| G16H 30/40 | (2018.01) | |

(52) U.S. Cl.
CPC ............ *G06T 7/0012* (2013.01); *G06T 7/168* (2017.01); *G06V 10/454* (2022.01); *G06V 10/764* (2022.01); *G06V 10/82* (2022.01); *G16H 30/40* (2018.01); *G06T 2207/10081* (2013.01); *G06T 2207/20081* (2013.01); *G06T 2207/20084* (2013.01); *G06T 2207/30036* (2013.01)

(58) Field of Classification Search
CPC ... A61C 9/00; A61C 13/0004; A61C 13/0019; A61C 19/04; A61C 8/009; A61C 13/0013; A61C 13/08; A61C 19/10; A61C 9/0046; G06N 3/082; G06N 3/08; G06N 20/00; G06N 3/045; G06N 3/02; G06N 3/04; G06T 7/0012; G06T 7/168; G06T 2207/10081; G06T 2207/20081; G06T 2207/20084; G06T 2207/30036; G06T 7/11; G06T 17/00; G06T 2207/10028; G06T 19/20; G06T 2207/10024; G06T 2207/10012; G06T 7/344; G06T 7/136; G06T 7/00; G06T 7/187; G06T 2207/30008; G06T 2207/10116; G06T 2210/41; G06T 1/0007; G06T 15/00; G06T 2200/04; G06T 2207/10084; G06T 2207/20021; G06T 2207/30052; G06T 7/337; G06T 7/70; G06V 10/454; G06V 10/764; G06V 10/82; G06V 2201/033; G06V 10/75; G06V 2201/03; G16H 30/40; G16H 20/40; G16H 50/20; G16H 50/70; G16H 10/60; G16H 20/10; G16H 20/30; G16H 30/00; G16H 50/50; G16H 30/20; G06F 18/2414; A61B 5/0088; A61B 2018/20353; A61B 5/4547; A61B 5/004; A61B 5/4542; A61B 5/7203; A61B 5/7264; A61B 6/14; A61B 5/00; A61B 5/0033; A61B 6/4085; A61B 2034/108; A61B 34/10; A61B 5/7267; A61B 6/032; A61B 6/035; A61B 6/5217
See application file for complete search history.

(56) References Cited

U.S. PATENT DOCUMENTS

| | | |
|---|---|---|
| 8,099,305 B2 | 1/2012 | Kuo et al. |
| 8,135,569 B2 | 3/2012 | Matov et al. |
| 8,439,672 B2 | 5/2013 | Matov et al. |
| 8,639,477 B2 | 1/2014 | Chelnokov et al. |
| 9,107,722 B2 | 8/2015 | Matov et al. |
| 9,135,498 B2 | 9/2015 | Andreiko et al. |
| 9,904,999 B2 | 2/2018 | Andreiko et al. |
| 10,032,271 B2 | 7/2018 | Somasundaram et al. |
| 10,235,606 B2 | 3/2019 | Miao et al. |
| 10,456,229 B2 | 10/2019 | Fisker et al. |
| 10,610,185 B2 | 4/2020 | Taguchi et al. |
| 10,685,259 B2 | 6/2020 | Salah et al. |
| 10,932,890 B1 | 3/2021 | Sant et al. |
| 10,997,727 B2 | 5/2021 | Xue et al. |
| 11,007,036 B2 | 5/2021 | Pokotilov et al. |
| 11,107,218 B2 | 8/2021 | Salah et al. |
| 2005/0019732 A1 | 1/2005 | Kaufmann et al. |
| 2005/0192835 A1 | 9/2005 | Kuo et al. |
| 2008/0085487 A1 | 4/2008 | Kuo et al. |
| 2008/0253635 A1 | 10/2008 | Spies et al. |
| 2009/0191503 A1 | 7/2009 | Matov et al. |
| 2010/0069741 A1 | 3/2010 | Kuhn et al. |
| 2011/0038516 A1 | 2/2011 | Koehler et al. |
| 2011/0081071 A1 | 4/2011 | Benson et al. |
| 2011/0255765 A1 | 10/2011 | Carlson et al. |
| 2012/0063655 A1 | 3/2012 | Dean et al. |
| 2013/0022251 A1 | 1/2013 | Chen et al. |
| 2013/0039556 A1 | 2/2013 | Kachelriess et al. |
| 2013/0230818 A1 | 9/2013 | Matov et al. |
| 2014/0169648 A1* | 6/2014 | Andreiko ............... G16Z 99/00 382/128 |
| 2014/0227655 A1 | 8/2014 | Andreiko et al. |
| 2015/0029178 A1 | 1/2015 | Claus et al. |
| 2016/0008095 A1 | 1/2016 | Matov et al. |
| 2016/0034788 A1 | 2/2016 | Lin et al. |
| 2016/0042509 A1 | 2/2016 | Andreiko et al. |
| 2016/0078647 A1 | 3/2016 | Schildkraut et al. |
| 2016/0117850 A1 | 4/2016 | Jin et al. |
| 2016/0324499 A1 | 11/2016 | Sen Sharma et al. |
| 2016/0371862 A1 | 12/2016 | Silver et al. |
| 2017/0024634 A1 | 1/2017 | Miao et al. |
| 2017/0046616 A1 | 2/2017 | Socher et al. |
| 2017/0100212 A1 | 4/2017 | Sherwood et al. |
| 2017/0150937 A1 | 6/2017 | Stille et al. |
| 2017/0169562 A1 | 6/2017 | Somasundaram et al. |
| 2017/0265977 A1 | 9/2017 | Fisker et al. |
| 2017/0270687 A1 | 9/2017 | Manhart |
| 2018/0005377 A1* | 1/2018 | Alvarez ................... G06T 7/74 |
| 2018/0028294 A1* | 2/2018 | Azernikov ........ G06F 18/24143 |
| 2018/0110590 A1* | 4/2018 | Maraj ..................... A61C 7/002 |
| 2018/0182098 A1 | 6/2018 | Andreiko et al. |
| 2018/0253866 A1 | 9/2018 | Jain et al. |
| 2018/0300877 A1 | 10/2018 | Somasundaram et al. |
| 2019/0026599 A1 | 1/2019 | Salah et al. |
| 2019/0147245 A1 | 5/2019 | Qi et al. |
| 2019/0147666 A1* | 5/2019 | Keustermans .......... G06T 19/20 433/213 |
| 2019/0148005 A1* | 5/2019 | Domracheva ........... G06T 19/20 345/424 |
| 2019/0164288 A1 | 5/2019 | Wang et al. |
| 2019/0172200 A1 | 6/2019 | Andreiko et al. |
| 2019/0282333 A1 | 9/2019 | Matov et al. |
| 2019/0328489 A1 | 10/2019 | Capron-Richard et al. |
| 2020/0015948 A1 | 1/2020 | Fisker et al. |
| 2020/0022790 A1 | 1/2020 | Fisker |
| 2020/0085535 A1 | 3/2020 | Pokotilov et al. |
| 2020/0179089 A1 | 6/2020 | Serval et al. |
| 2020/0320685 A1 | 10/2020 | Anssari Moin et al. |
| 2021/0045843 A1 | 2/2021 | Pokotilov et al. |
| 2021/0082184 A1 | 3/2021 | Claessen et al. |
| 2021/0110584 A1 | 4/2021 | Claessen et al. |
| 2021/0150702 A1 | 5/2021 | Claessen et al. |
| 2021/0174543 A1 | 6/2021 | Claessen et al. |
| 2021/0217233 A1 | 7/2021 | Feng et al. |
| 2021/0264611 A1 | 8/2021 | Xue et al. |
| 2022/0067943 A1 | 3/2022 | Claessen et al. |
| 2023/0186476 A1 | 6/2023 | Ghazvinian Zanjani et al. |
| 2023/0263605 A1 | 8/2023 | Madden et al. |

FOREIGN PATENT DOCUMENTS

| | | |
|---|---|---|
| CN | 108205806 A | 6/2018 |
| CN | 108305684 A | 7/2018 |

(56) References Cited

FOREIGN PATENT DOCUMENTS

| | | | |
|---|---|---|---|
| EP | 2742857 A1 | 6/2014 |
| EP | 3121789 A1 | 1/2017 |
| EP | 3462373 A1 | 4/2019 |
| EP | 3591616 A1 | 1/2020 |
| EP | 3671531 A1 | 6/2020 |
| EP | 3767521 A1 | 1/2021 |
| JP | 2007-525289 A | 9/2007 |
| JP | 2010-220742 A | 10/2010 |
| JP | 2013-537445 A | 10/2013 |
| JP | 2017-102622 A | 6/2017 |
| JP | 2017-520292 A | 7/2017 |
| JP | 2017-157138 A | 9/2017 |
| JP | 2022-501299 A | 1/2022 |
| WO | 2015169910 A1 | 11/2015 |
| WO | 2016143022 A1 | 9/2016 |
| WO | 2017099990 A1 | 6/2017 |
| WO | 2019002616 A1 | 1/2019 |
| WO | 2019002631 A1 | 1/2019 |
| WO | 2019068741 A2 | 4/2019 |
| WO | 2019122373 A1 | 6/2019 |
| WO | 2019207144 A1 | 10/2019 |
| WO | 2020007941 A1 | 1/2020 |
| WO | 2020127398 A1 | 6/2020 |
| WO | 2021009258 A1 | 1/2021 |

OTHER PUBLICATIONS

Hosntalab et al. "A Hybrid Segmentation Framework for Computer-Assisted Dental Procedures", IEICE Transactions on Information and Systems, Oct. 2009, pp. 2137-2151, vol. E92D, No. 10.

Studholme et al. "Automated Three-Dimensional Registration of Magnetic Resonance and Positron Emission Tomography Brain Images by Multiresolution Optimization of Voxel Similarity Measures", Medical Physics, 1997, pp. 25-35, vol. 24. No. 1.

Ahn, B, "The Compact 3D Convolutional Neural Network for Medical Images", Jul. 2, 2017, pp. 1-9, http://cs231n.standord.edu/reports/2017/pdfs/23/pdf, retrieved Dec. 18, 2018.

Auro Tripathy, "Five Insights from GoogLeNet You Could Use in Your Own Deep Learning Nets", Sep. 20, 2016, pp. 1-21, https://www.slideshare.net/aurot/googlenet-insights?from_action=save, retrieved Dec. 18, 2018.

Bustos et al., "An Experimental Comparison of Feature-Based 3D Retrieval Methods" 2nd International Symposium on 3D Data Processing, Visualization, and Transmission, 3DPVT 2004, Sep. 6-9, 2004, pp. 215-222.

Chaouch, M. and Verroust-Blondet, A., "Alignment of 3D Models", Graphical Models, Mar. 2009, pp. 63-76, vol. 71, No. 2.

Çiçek et al., "3D U-Net: Learning Dense Volumetric Segmentation from Sparse Annotation", Medical Image Computing and Computer-Assisted Intervention—MICCAI 2016, Part II, Oct. 2, 2016, pp. 424-432.

Duda et al., "Pattern Classification: Introduction", 2001, Pattern Classification, New York, John Wiley & Sons, US, pp. 1-13.

Duy et al., "Automatic Detection and Classification of Teeth in CT Data", International Conference on Medical Image Computing and Computer-Assisted Intervention—MICCAI 2012, 2012, pp. 609-616.

Everingham et al., "The PASCAL Visual Object Classes (VOC) Challenge", International Journal of Computer Vision, Sep. 9, 2009, pp. 303-338, vol. 88, No. 2.

Fechter et al., "A 3D Fully Convolutional Neural Network and a Random Walker to Segment the Esophagus in CT", Apr. 21, 2017, 23 pages, https://arxiv.org/pdf/1704.06544.pdf, retrieved Dec. 18, 2018.

Gjesteby et al., "Deep Learning Methods for CT Image-Domain Metal Artifact Reduction", SPIE, Developments in X-Ray Tomography XI, Sep. 25, 2017, 6 pages, vol. 10391.

Gkantidis et al. "Evaluation of 3-Dimensional Superimposition Techniques on Various Skeletal Structures of the Head Using Surface Models", PLOS ONE, Feb. 23, 2015, 20 pages, vol. 10, No. 2.

Hall, P. and Owen, M. "Simple Canonical Views", Proceedings of the British Machine Vision Conference (BMVC), Sep. 2005, 10 pages.

Han et al., "Deep Residual Learning for Compressed Sensing CT Reconstruction Via Persistent Homology Analysis", Cornell University Library, Nov. 19, 2016, pp. 1-10.

He et al., "Deep Residual Learning for Image Recognition", 2016 IEEE Conference on Computer Vision and Pattern Recognition (CPR), Jun. 2016, pp. 770-778.

Hongming Li, Y. "Non-Rigid Image Registration Using Fully Convolutional Networks With Deep Self-Supervision", Sep. 3, 2017, 8 pages.

Isola et al., "Image-to-Image Translation with Conditional Adversarial Networks", 2017 IEEE Conference on Computer Vision and Pattern Recognition (CVPR), Honolulu, HI, 2017, pp. 5967-5976.

Joda, T. and Gallucci, G. "Systematic Literature Review of Digital Three-Dimensional Superimposition Techniques to Create Virtual Dental Patients", The International Journal of Oral & Maxillofacial Implants, 2015, pp. 330-337, vol. 30, No. 2.

Jung et al., "Combining Volumetric Dental CT and Optical Scan Data for Teeth Modeling", Computer-Aided Design, Oct. 2015, pp. 24-37, vol. 67-68.

Klinder et al., "Automated Model-Based Vertebra Detection, Identification, and Segmentation in CT Images", Medical Image Analysis, Jun. 2009, pp. 471-482, vol. 13, No. 3.

Li et al., "PointCNN: Convolution on X-Transformed Points", Neural Information Processing Systems (NIPS), Nov. 5, 2018, 11 pages.

Liao et al. "Automatic Tooth Segmentation of Dental Mesh Based on Harmonic Fields", Biomedical Research International, 2015, 10 pages, vol. 2015.

Litjens et al. "A Survey on Deep Learning in Medical Image Analysis", Medical Image Analysis, Dec. 2017, pp. 60-88, vol. 42.

Meyer et al. "Normalized Metal Artifact Reduction (NMAR) in Computed Tomography", Medical Physics, Oct. 2010, pp. 5482-5493, vol. 37, No. 10.

Miki et al. "Tooth Labeling in Cone-Beam CT Using Deep Convolutional Neural Network for Forensic Identification", SPIE 10134, Medical Imaging 2017: Computer-Aided Diagnosis, Mar. 3, 2017, 6 pages.

Miki et al. "Classification of Teeth in Cone-Beam CT Using Deep Convolutional Neural Network", Computers in Biology and Medicine, Jan. 2017, pp. 24-29, vol. 1, No. 80.

Pavaloiu et al., "Automatic Segmentation for 3D Dental Reconstruction", IEEE 6th ICCCNT, Jul. 13-15, 2015, 6 pages.

Pavaloiu et al., "Neural Network Based Edge Detection for CBCT Segmentation", 5th IEEE EHB, Nov. 19-21, 2015.

Qi et al., "PointNet: Deep Learning on Point Sets for 3D Classification and Segmentation", Computer Vision and Pattern Recognition (CVPR), 2017, 19 pages.

Ruellas et al. "3D Mandibular Superimposition: Comparison of Regions of Reference for Voxel-Based Registration" PLOS ONE, Jun. 23, 2016, 13 pages.

Ryu et al. "Analysis of Skin Movement With Respect to Flexional Bone Motion Using MR Images of a Hand", Journal of Biomechanics, 2006, pp. 844-852, vol. 39, No. 5.

Schulze et al., "Artefacts in CBCT: A Review", Dentomaxillofacial Radiology, Jul. 1, 2011, pp. 265-273, vol. 40, No. 5.

Sekuboyina et al., "A Localisation-Segmentation Approach for Multi-Label Annotation of Lumbar Vertebrae Using Deep Nuts", Cornell University Library, 201 Olin Library Cornell University Ithaca, NY 14853, Mar. 13, 2017, 10 pages.

Simonovsky et al. "A Deep Metric for Multimodal Registration" International Conference on Medical Image Computing and Computer-Assisted Intervention (MICCAI), 2016, pp. 10-18, vol. 9902.

Szegedy et al., "Going Deeper With Convolutions", 2015 IEEE Conference on Computer Vision and Pattern Recognition (CVPR), Jun. 2015, pp. 1-9.

Tonioni et al., "Learning to Detect Good 3D Keypoints", International Journal of Computer Vision, 2018, pp. 1-20, vol. 126.

Wang et al., "Dynamic Graph CNN for Learning on Point Clouds", ACM Trans. Graph, Jan. 2019, vol. 1, No. 1, 13 pages.

(56) References Cited

OTHER PUBLICATIONS

Wu et al. "Tooth Segmentation on Dental Meshes Using Morphologic Skeleton", Computers & Graphics, Feb. 2014, pp. 199-211, vol. 38.
Wu et al., "Model-Based Teeth Reconstruction", ACM Transactions on Graphics (TOG), ACM, US, Nov. 11, 2016, pp. 1-13, vol. 35, No. 6.
Yau et al., "Tooth Model Reconstruction Based Upon Data Fusion for Orthodontic Treatment Simulation", Computers in Biology and Medicine, May 1, 2014, pp. 8-16, vol. 48.
Yu, Y. "Machine Learning for Dental Image Analysis", Nov. 2016, 61 pages, https://arxiv.org/ftp/arxiv/papers/1611/1611.09958.pdf, retrieved Nov. 30, 2017.
Zhang, Y. and Yu, H., "Convolutional Neural Network Based Metal Artifact Reduction in X-Ray Computed Tomography", IEEE Transactions on Medical Imaging, Jun. 2018, pp. 1370-1381, vol. 37, No. 6.
Zhang, C. and Xing, Y., "CT Artifact Reduction Via U-Net CNN", SPIE, Medical Imaging 2018: Image Processing, Mar. 2, 2018, 6 pages, vol. 10574.
International Search Report and Written Opinion for International Patent Application No. PCT/EP2019/073438, dated Nov. 20, 2019.
Office Action in corresponding Chinese Patent Application No. 201980057692.4 dated Aug. 27, 2021.
Chen et al. "Deep RBFNet: Point Cloud Feature Learning Using Radial Basis Functions", Cornell University Library, Dec. 11, 2018, 11 pages.
Chen et al. "Fast Resampling of 3D Point Clouds Via Graphs", IEEE Transactions on Signal Processing, Feb. 1, 2018, pp. 666-681, vol. 66, No. 3.
Eun, H. and Kim, C. "Oriented Tooth Localization for Periapical Dental X-ray Images via Convolutional Neural Network", Asia-Pacific Signal and Information Processing Association Annual Summit and Conference (APSIPA), Dec. 3, 2016, pp. 1-7.
Fang et al. "3D Deep Shape Descriptor", 2015 IEEE Conference on Computer Vision and Pattern Recognition (CVPR), 2015, pp. 2319-2328.
Ghafoorian et al. "EL-GAN: Embedding Loss Driven Generative Adversarial Networks for Lane Detection", Computer Vision—ECCV 2018 Workshops, Jan. 23, 2019, pp. 256-272, vol. 11129.
Ghazvinian Zanjani et al. "Deep Learning Approach to Semantic Segmentation in 3D Point Cloud Intra-oral Scans of Teeth", Proceedings of the 2nd International Conference on Medical Imaging with Deep Learning, 2019, 22 pages, retrieved online from https://openreview.net/forum?id=ByxLSoblgV.
Gomes et al. "Efficient 3D Object Recognition Using Foveated Point Clouds", Computers & Graphics, May 1, 2013, pp. 496-508, vol. 37.
Gorler, O. and Akkoyun, S. "Artificial Neural Networks Can be Used as Alternative Method to Estimate Loss Tooth Root Sizes for Prediction of Dental Implants", Cumhuriyet University Faculty of Science Science Journal (CSJ), Apr. 2017, pp. 385-395, vol. 38, No. 2.
Guo et al. "3D Mesh Labeling Via Deep Convolutional Neural Networks", ACM Transactions on Graphics, Dec. 2015, pp. 1-12, vol. 35, No. 1, Article 3.
Hermosilla et al. "Monte Carlo Convolution for Learning on Non-Uniformly Shaped Point Clouds", ACM Transactions on Graphics, Nov. 2018, 12 pages, vol. 37, No. 6, Article 235.
Hou et al. "3D-SIS: 3D Semantic Instance Segmentation of RGB-D Scans", Computer Vision and Pattern Recognition (CPR), Apr. 29, 2019, 14 pages.
Huang et al. "Edge-Aware Point Set Resampling", ACM Transactions on Graphics, 2013, pp. 1-12, vol. 32, No. 1, Article 9.
Johari et al. "Detection of Vertical Root Fractures in Intact and Endodontically Treated Premolar Teeth by Designing a Probabilistic Neural Network: An ex vivo Study", Dentomaxillofacial Radiology, Feb. 2017, vol. 46, No. 2, pp. 1-9.
Ku et al. "Joint 3D Proposal Generation and Object Detection from View Aggregation", IEEE/RSJ International Conference on Intelligent Robots and Systems (IROS), Jul. 12, 2018, pp. 1-8.
Le T. and Duan Y. "PointGrid: A Deep Network for 3D Shape Understanding", Proceedings of the IEEE Conference on Computer Vision and Pattern Recognition, Jun. 18-23, 2018, pp. 9204-9214.
Li et al. "SO-Net: Self-Organizing Network for Point Cloud Analysis", Eye In-Painting with Exemplar Generative Adversarial Networks, Jun. 2018, pp. 9397-9406.
Liu, C. and Furukawa, Y. "MASC: Multi-scale Affinity with Sparse Convolution for 3D Instance Segmentation", Computer Vision and Pattern Recognition (CPR), Feb. 12, 2019, 4 pages.
Qi et al. "Frustum PointNets for 3D Object Detection from RGB-D Data", Computer Vision and Pattern Recognition (CPR), Apr. 13, 2018, 15 pages.
Qi et al. "PointNet++: Deep Hierarchical Feature Learning on Point Sets in a Metric Space", Conference on Neural Information Processing Systems (NIPS), Jun. 2017, 14 pages.
Ravanbakhsh et al. "Deep Learning With Sets and Point Clouds", Feb. 24, 2017, 12 pages, retrieved online from https://arxiv.org/abs/1611.04500.
Silva et al. "Automatic Segmenting Teeth in X-Ray Images: Trends, A Novel Data Set, Benchmarking and Future Perspectives", Feb. 9, 2018, 33 pages, retrieved online from https://arxiv.org/pdf/1802.03086.pdf.
Skrodzki et al. "Directional Density Measure to Intrinsically Estimate and Counteract Non-Uniformity in Point Clouds", Computer Aided Geometric Design, Aug. 2018, pp. 73-89, vol. 64.
Shaoqing et al. "Mask R-CNN", Proceedings of the IEEE International Conference on Computer Vision, 2017, pp. 2961-2969.
Tian, S. "Automatic Classification and Segmentation of Teeth on 3D Dental Model Using Hierarchical Deep Learning Networks" IEEE Journals & Magazine, Jun. 21, 2019, pp. 84817-84828.
Wang et al. "SGPN: Similarity Group Proposal Network for 3D Point Cloud Instance Segmentation", CVF Conference on Computer Vision and Pattern Recognition, Nov. 23, 2017, 13 pages.
Wu et al. "3D ShapeNets: A Deep Representation for Volumetric Shapes", 2015 IEEE Conference on Computer Vision and Pattern Recognition (CVPR), 2015, pp. 1912-1920.
Xu et al. "SpiderCNN: Deep Learning on Point Sets with Parameterized Convolutional Filters", Computer Vision—EECV, 2018, 16 pages.
Yi et al. "GSPN: Generative Shape Proposal Network for 3D Instance Segmentation in Point Cloud", Proceedings of the IEEE/CVF Conference on Computer Vision and Pattern Recognition (CVPR), 2019, 13 pages.
Zhou et al. "A Method for Tooth Model Reconstruction Based on Integration of Multimodal Images", Journal of Healthcare Engineering, Jun. 20, 2018, vol. 8, pp. 1-8.
Non-published U.S. Appl. No. 17/415,465, filed Jun. 17, 2021.
Non-published U.S. Appl. No. 17/626,744, filed Jan. 12, 2022.
Atzmon et al. "Point Convolutional Neural Networks by Extension Operators", Mar. 27, 2018, 14 pages, arXiv:1803.10091v1 [cs.CV].
Office Action in corresponding Japanese application Ser. No. 2021-510643 dated Oct. 2, 2023.
Hamida et al. "Deep Learning for Semantic Segmentation of Remote Sensing Images with Rich Spectral Content", 2017 IEEE International Geoscience and Remote Sensing Symposium (IGARSS), 2017, pp. 2569-2572.
Kamnitsas et al. "Efficient Multi-scale 3D CNN With Fully Connected CRF for Accurate Brain Lesion Segmentation", Medical Image Analysis, 2017, pp. 61-78, vol. 36.

\* cited by examiner

AUTOMATED ORTHODONTIC TREATMENT PLANNING USING DEEP LEARNING

CROSS-REFERENCE TO RELATED APPLICATION

The present application is a national stage of and claims priority of International patent application Serial No. PCT/EP2019/073438, filed Sep. 3, 2019, and published in English as WO2020/048960A1.

FIELD OF THE INVENTION

The invention relates to an automated system for determining an orthodontic treatment plan.

The invention further relates to an automated method of determining an orthodontic treatment plan and a method of training a deep neural network.

The invention also relates to a computer program product enabling a computer system to perform such methods.

BACKGROUND OF THE INVENTION

Orthodontic treatment results in a patient's teeth being moved from an initial position, i.e. the position before the treatment is started, to a desired position in order to move the teeth into proper alignment. Traditionally, orthodontic treatment was performed using braces, involving wires and metal brackets. Braces need to be adjusted by an orthodontist several times. Nowadays, the use of a sequence of aligners, i.e. a series of templates, is a popular choice due to its aesthetics and comfort.

For the purpose of this disclosure, 'tooth' refers to a whole tooth including crown and root, 'teeth' refers to any set of teeth consisting of two or more teeth, whereas a set of teeth originating from a single person will be referred to as originating from a 'dentition'. A dentition may not necessarily contain the total set of teeth from an individual. Further, 'classification' refers to identifying to which of a set of categories an observation or sample belongs. In the case of tooth classification, "classification" refers to the process of identifying to which category (or label) a single tooth belongs and in particular to the process of deriving labels for all individual teeth from a single dentition. 3D data set refers to any digital representation of any dentition, e.g. a 3D voxel representation of a filled volume, densities in a volume, a 3D surface mesh, etc.

A method for providing dynamic orthodontic assessment and treatment profiles exists. As initial step of the method, a mold or a scan of a patient's teeth crowns or mouth tissue is acquired. From the data so obtained, a digital data set is derived that represents the initial arrangement of each of the patient's teeth crowns (excluding teeth roots) and of gum tissue surrounding the patient's teeth. The desired final position of each of the teeth can be received from a clinician in the form of a prescription, can be calculated from basic orthodontic principles, or can be extrapolated computationally from a clinical prescription.

In order to determine segmented paths (i.e. incremental movements to intermediate positions over time) for each of the teeth crowns, a finite element model of an in-place aligner is created and finite element analysis is applied. Inputs to the process include an initial aligner shape, digital models of the teeth in position in the jaw and models of the jaw tissue (i.e. the gum tissue surrounding the patient's teeth). At various stages of the process, and in particular after the segmented paths have been defined, the process can, and generally will, interact with a clinician for the treatment of the patient. A client process is advantageously programmed to display an animation of the positions and paths and to allow the clinician to reset the final positions of one or more of the teeth crowns and to specify constraints to be applied to the segmented paths. A dental data mining system, e.g. comprising a neural network, is used to determine whether determined motions are orthodontically acceptable and whether a determined candidate aligner is the best solution so far.

A drawback of the method above is that the orthodontic treatment plan will normally need to be updated at least once during the treatment and likely even more often. Thus, regular interaction with a clinician is still required in order to make the patient's teeth move to their desired position.

SUMMARY OF THE INVENTION

The first object of the invention is to provide an automated system for determining an orthodontic treatment plan, which requires limited or no interaction with a clinician (apart from uploading and downloading data) and which can automatically determine a plan whose execution requires limited or no interaction with a clinician.

The second object of the invention is to provide an automated method of determining an orthodontic treatment plan, which requires limited or no interaction with a clinician (apart from uploading and downloading data) and which can be used to automatically determine a plan whose execution requires limited or no interaction with a clinician.

In a first aspect of the invention, a system comprises at least one processor configured to obtain a plurality of training dental computed tomography scans which reflect a moment before respective successful orthodontic treatments, identify individual teeth and jaw bone in each of said training dental computed tomography scans, and train a deep neural network with training input data obtained from said plurality of training dental computed tomography scans and training target data per training dental computed tomography scan to determine a desired final position, and optionally an attachment type, per tooth from input data obtained from a patient dental computed tomography scan, wherein input training data obtained from a training dental computed tomography scan represents all teeth and the entire alveolar process and identifies said individual teeth and said jaw bone.

The training data could comprise an image data set representing an entire computed tomography scan, as originally produced by the CT scanner, along with information delineating the individual teeth and the jaw for each of the training dental computed tomography scans, but as such computed tomography scans of a sufficiently accurate voxel resolution are quite large, it is preferable to instead include 3D data, e.g. comprising meshes, point clouds or voxels (in particular, a subset of voxels representing only the relevant structures). The training data could comprise a single 3D data set representing an entire computed tomography scan along with information delineating the individual teeth and the jaw for each of the training dental computed tomography scans.

Alternatively, the training data could comprise multiple 3D data sets, e.g. one for each tooth and one for the jaw bone. In the case that training 3D data sets include data sourced from an optical scan of the actual tooth, the training data will be highly accurate without required interpretation of the (e.g. voxel) data by an expert. 3D data sets of complete teeth may also be merged with e.g. intra-oral scans (also being 3D data sets), potentially yielding higher spatial resolution 3D data of the crown sections as derived from the intra-oral scan. The obtained plurality of training dental computed tomography scans may comprise scans as originally produced by the CT scanner or may comprise 3D data sets created therefrom. The obtained plurality of training dental computed tomography scans may be entirely included in the training data.

A jaw comprises teeth and jaw bone. The jaw bone comprises the alveolar process and the basal bone. The alveolar process comprises the tooth sockets and the thickened ridge of bone that contains the tooth sockets. The dentoalveolar complex comprises the teeth, the alveolar process and the gum, but not the basal bone. The training data obtained from a training dental computed tomography scan may represent other parts of the dentoalveolar complex in addition to all teeth and the entire alveolar process and may even represent the entire dentoalveolar complex.

The inventors have recognized that the method disclosed in US 2017/0100212 does not take sufficient information into account, which may result in the determination of a desired final position per tooth that is in reality not achievable and therefore requires interaction with a clinician to adjust the desired final tooth positions and therefore the orthodontic treatment plan. By using (CB)CT data, identifying individual teeth (including root) and jaw bone (including outer boundaries) and using training data that represents all teeth and the entire dentoalveolar process, the 3D image data and dento-physical properties may be utilized to encode relevant (deriviations of) information in the deep neural network and as a result, desired final positions may be determined that do not need to be adjusted by a clinician.

The dento-physical properties may comprise the physical conditions and restraints of the teeth and the bony housing (the dento-alveolar complex), for example. The physical conditions may comprise, for example, an amount of contact area, e.g. between teeth and bone. Properties of the teeth and the bony housing may yield a maximum movement of the teeth over time and/or a maximum amount of overlap between two volumes. The identification of the individual teeth may be used by the deep neural network to encode any such general and geometry-specific information as may be identified from training data. By utilizing the information from the identification, the applicable aspects of this information will be encoded, e.g. potentially per individual tooth, in the trained network and thus will be employed when utilizing the trained network during a prediction (or inference) stage.

The desired final position per tooth is often determined by a clinician, but it is beneficial to be able to do this automatically. In this case, no interaction with a clinician is required or the clinician only needs to perform a short check of the determined desired final positions. If the desired final positions are determined automatically, but without considering sufficient information, then the clinician will normally notice this during the treatment and determine the desired final positions himself (i.e. override the automatically determined desired final positions).

Said at least one processor may be configured to use said identification of said individual teeth and said jaw bone to determine dento-physical properties (e.g. per tooth) for each of said training dental computed tomography scans and to facilitate the encoding of information reflecting said dento-physical properties in said deep neural network. By incorporating knowledge considering the dento-physical properties during training of the deep neural network, the problem definition is more complete and the results have the potential to become highly accurate and feasible as a result. Said dento-physical properties may be encoded in said deep neural network by training said deep neural network with a loss function which depends on said determined dento-physical properties.

Said training data obtained from said training dental computed tomography scan may further represent all basal bone. The dento-physical properties may then include at least one property be related to skeletal relationships, for example.

One or more of said plurality of training dental computed tomography scans may be associated with an indicator indicating an achieved transformation per tooth and/or an indicator indicating an attachment type per tooth, said transformation comprising a translation and/or a rotation per tooth (e.g. a transformation matrix or a vector) and said indicators being included in said training target data. These indicators are advantageous training targets. The indicator indicating the achieved transformation per tooth allows the deep neural network to determine a transformation per tooth for a patient dental computed tomography scan and allows the desired final position per tooth to be determined based on this determined transformation. Applying the indicator indicating the transformation to data obtained from a dental computed tomography scan from before a successful orthodontic treatment would normally result in data obtained from a dental computed tomography scan from after the successful orthodontic treatment. The indicator indicating the attachment type per tooth allows the deep neural network to determine an applicable attachment type per tooth for a patient dental computed tomography, which can additionally be used to create three-dimensional models of aligners.

One or more of said plurality of training dental computed tomography scans which reflect a moment before respective successful orthodontic treatments may each be associated with data obtained from a further training dental computed tomography scan, said further training dental computed tomography scan reflecting a moment after a corresponding successful orthodontic treatment and being included in said training target data. Instead of the indicator indicating a transformation, a patient dental CT scan before the orthodontic treatment and a patient dental CT scan after the orthodontic treatment may be included in the training data to allow the system to determine the transformation automatically, for example.

Said at least one processor may be configured to obtain at least one of said one or more training dental computer tomography scans by transforming data resulting from one of said further training dental computed tomography scans. This may be used to automatically generate training data purely based on 'correct' dentitions.

These 'correct' dentitions are not necessarily the result of orthodontic treatments but could belong to persons born who have a 'correct' dentition naturally. It may even be possible to train the deep neural network without data/CT scans from after an orthodontic treatment.

In a second aspect of the invention, a system comprises at least one processor configured to obtain a patient dental computed tomography scan, identify individual teeth and jaw bone in said patient dental computed tomography scan, and use said deep neural network to determine a desired final position, and optionally an attachment type, per tooth from input data obtained from said patient dental computed tomography scan, wherein said input data represents all teeth and the entire alveolar process and identifies said individual teeth and said jaw bone. Said determined desired final positions are used to determine a sequence of desired intermediate positions per tooth and said determined intermediate positions and said determined final positions, and optionally attachment types, are used to create three-dimensional representations of teeth and/or aligners.

The three-dimensional representations may comprise voxels, meshes or point clouds, for example. The three-dimensional representations may be stored in STL or VRML format as 3D models, for example. The three-dimensional representations of the aligners may be usable by a 3D printer to print the aligners or to print intermediate structures from which aligners may be created.

The input data could comprise an image data set representing an entire computed tomography scan, as originally produced by the CT scanner, along with information delineating the individual teeth and the jaw, but as such computed tomography scans of a sufficiently accurate voxel resolution are quite large, it is preferable to instead include 3D data, e.g. comprising meshes, point clouds or voxels (in particular, a subset of voxels representing only the relevant structures). The input data could comprise a single 3D data set representing an entire computed tomography scan along with information delineating the individual teeth and the jaw. Alternatively, the input data could comprise multiple 3D data sets, e.g. one for each tooth and one for the jaw bone. The obtained patient dental computed tomography scans may comprise a scan as originally produced by the CT scanner or may comprise 3D models created therefrom. The obtained patient dental computed tomography scan may be entirely included in the input data.

Said at least one processor may be configured to determine said sequence of desired intermediate positions per tooth based on said determined desired final positions and to create said three-dimensional representations of said aligners or to create intermediate three-dimensional representations for the purpose of manufacturing said aligners, based on said determined intermediate and final positions and optionally attachment types per tooth. An intermediate model for such purpose may e.g. represent teeth and/or additional 3D volumes such as gingiva, attachments, in intermediate or final positions, which may be 3D printed and used as a negative template for the creation of an aligner, e.g. by means of vacuum forming. Alternatively, said sequence of desired intermediate positions per tooth and said three-dimensional representations of said aligners or said intermediate three-dimensional representations may be determined by a different system.

Said at least one processor may be configured to determine three-dimensional representations of said teeth in each of said intermediate and final positions, and optionally of said attachment types per tooth, and create said three-dimensional representations of said aligners or create intermediate three-dimensional representations for creating such aligners based on said three-dimensional representations of said teeth in each of said intermediate and final positions. The three-dimensional representations of the teeth may comprise voxels, meshes or point clouds, for example. The three-dimensional representations of the aligners may e.g. be created by utilizing the inverse of the volume representing the teeth, for example.

Said at least one processor may be configured to create said three dimensional representations of said teeth further based on data relating to tooth crowns obtained from an intraoral scan. Said at least one processor may be configured to create a superimposition of data relating to tooth crowns obtained from an intra oral scan on data obtained from said patient dental computed tomography scan and include said superimposition in said input data. This is beneficial, because an intraoral scan normally has a higher spatial resolution than a computed tomography scan. The higher resolution of the intraoral scan is advantageous when aligners are designed.

Said individual teeth and said jaw bone may be identified from said computer tomography scan using one or more further deep neural networks. A deep neural network allows the individual teeth and the jaw bone to be identified with appropriate accuracy. For example, a first further deep neural network may be used to segment a (CB)CT scan or intraoral scan into representations of (parts of) individual teeth and a second further deep neural network may be used to determine labels for the segmented teeth.

In a third aspect of the invention, a method of training a deep neural network comprises obtaining a plurality of training dental computed tomography scans which reflect a moment before respective successful orthodontic treatments, identifying individual teeth and jaw bone in each of said training dental computed tomography scans, and training a deep neural network with training input data obtained from said plurality of training dental computed tomography scans and training target data per training dental computed tomography scan to determine a desired final position, and optionally an attachment type, per tooth from input data obtained from a patient dental computed tomography scan, wherein training input data obtained from a training dental computed tomography scan represents all teeth and the entire alveolar process and identifies said individual teeth and said jaw bone.

In a fourth aspect of the invention, a method of determining an orthodontic treatment plan comprises obtaining a patient dental computed tomography scan, identifying individual teeth and jaw bone in said patient dental computed tomography scan, and using a deep neural network trained with said method of training a deep neural network to determine a desired final position, and optionally an attachment type, per tooth from input data obtained from said patient dental computed tomography scan, wherein said input data represents all teeth and the entire alveolar process and identifies said individual teeth and said jaw bone. Said determined desired final positions are used to determine a sequence of desired intermediate positions per tooth and said determined intermediate positions and said determined final positions, and optionally attachment types, are used to create three-dimensional representations of teeth and/or aligners or intermediate three-dimensional representations of structures for the creation of such aligners.

Moreover, a computer program for carrying out the methods described herein, as well as a non-transitory computer readable storage-medium storing the computer program are provided. A computer program may, for example, be downloaded by or uploaded to an existing device or be stored upon manufacturing of these systems.

A non-transitory computer-readable storage medium stores at least a first software code portion, the first software code portion, when executed or processed by a computer, being configured to perform executable operations comprising: obtaining a plurality of training dental computed tomography scans which reflect a moment before respective successful orthodontic treatments, identifying individual teeth and jaw bone in each of said training dental computed tomography scans, and training a deep neural network with training input data obtained from said plurality of training dental computed tomography scans and training target data per training dental computed tomography scan to determine a desired final position, and optionally an attachment type, per tooth from input data obtained from a patient dental computed tomography scan, wherein training input data obtained from a training dental computed tomography scan represents all teeth and the entire alveolar process and identifies said individual teeth and said jaw bone.

A non-transitory computer-readable storage medium stores at least a second software code portion, the second software code portion, when executed or processed by a computer, being configured to perform executable operations comprising: obtaining a patient dental computed tomography scan, identifying individual teeth and jaw bone in said patient dental computed tomography scan, and using a deep neural network trained with said method of training a deep neural network to determine a desired final position, and optionally an attachment type, per tooth from input data obtained from said patient dental computed tomography scan, wherein said input data represents all teeth and the entire alveolar process and identifies said individual teeth and said jaw bone. Said determined desired final positions are used to determine a sequence of desired intermediate positions per tooth and said determined intermediate positions and said determined final positions, and optionally attachment types, are used to create three-dimensional representations of teeth and/or aligners or intermediate three-dimensional representations of structures for the creation of such aligners.

As will be appreciated by one skilled in the art, aspects of the present invention may be embodied as a device, a method or a computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit", "module" or "system." Functions described in this disclosure may be implemented as an algorithm executed by a processor/microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium may include, but are not limited to, the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present invention, a computer readable storage medium may be any tangible medium that can contain, or store, a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including an object-oriented programming language such as Python, Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or a central processing unit (CPU), graphics processing unit (GPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of devices, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

BRIEF DESCRIPTION OF THE DRAWINGS

These and other aspects of the invention are apparent from and will be further elucidated, by way of example, with reference to the drawings, in which.

Corresponding elements in the drawings are denoted by the same reference numeral.

DETAILED DESCRIPTION OF THE DRAWINGS

Figure 1:
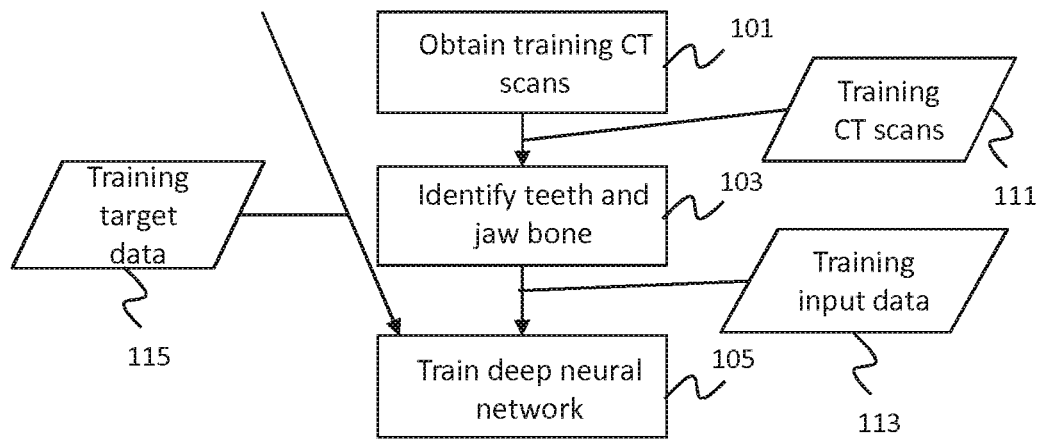
FIG. 1 shows a flow diagram of a first embodiment of the method of training a deep neural network of the invention.

A first embodiment of the method of training a deep neural network of the invention is shown in FIG. 1. A step 101 comprises obtaining a plurality of training dental computed tomography scans 111 which reflect a moment before respective successful orthodontic treatments. Training dental computed tomography scans 111 may be the scans originally produced by a (CB)CT scanner or voxel representations derived therefrom, for example. A step 103 comprises identifying individual teeth and jaw bone in each of the training dental computed tomography scans 111. This identification is included in training input data 113. This training input data 113 further includes data representing all teeth and the entire alveolar process, which may be the training dental computed tomography scans 111, parts thereof or 3D data sets derived therefrom. A step 105 comprises training a deep neural network with the training data 113 and target training data 115 per CT scan.

Figure 2:
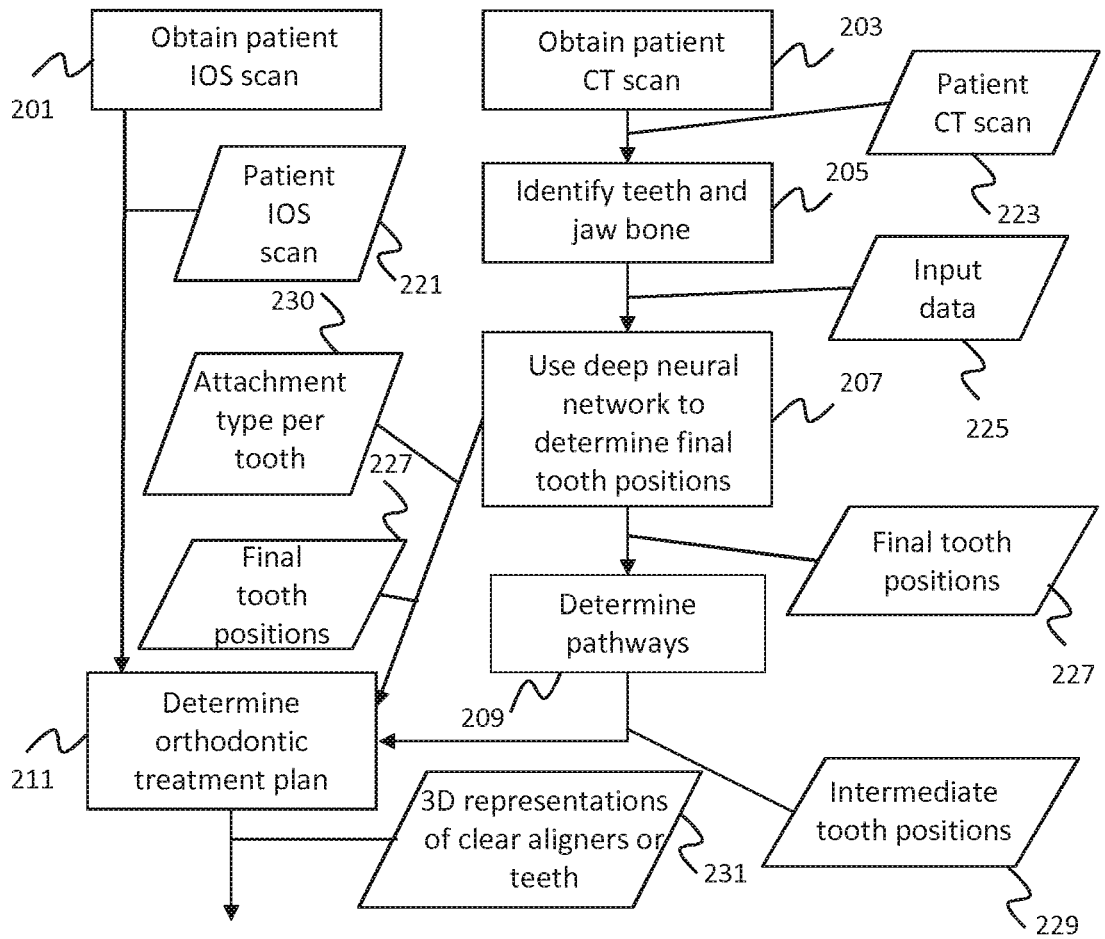
FIG. 2 shows a flow diagram of a first embodiment of the method of determining an orthodontic treatment plan of the invention.

A first embodiment of the method of determining an orthodontic treatment plan is shown in FIG. 2. A step 203 comprises obtaining a patient dental computed tomography scan 223. Patient dental computed tomography scan 223 may be a scan originally produced by a (CB)CT scanner or voxel representations derived therefrom, for example. A step 205 comprises identifying individual teeth and jaw bone in the patient dental computed tomography scan. This identification is included in input data 225. This input data 225 further includes data representing all teeth and the entire alveolar process, which may be the patient dental computed tomography scan 223, parts thereof or one or more 3D data sets derived therefrom.

A step 207 comprises using the deep neural network trained using the method of FIG. 1 to determine a desired final position per tooth from the input data 225, resulting in determined final tooth positions 227. If another algorithm is used to determine the desired final tooth positions as well, the output of this algorithm may be verified with the methods of the invention. The determined final tooth positions 227 may be compared with final tooth positions determined by this other algorithm, either inside or outside the deep neural network. In the former case, the deep neural network may indicate whether the two sets of final tooth positions are sufficiently similar, i.e. whether the final tooth positions determined by the other algorithm, provided as input to the deep neural network, have been verified. The determined desired final positions per tooth 227 are used to determine a sequence of desired intermediate positions per tooth 229, and thereby to determine the pathway per tooth. The determined intermediate positions 229 and determined final positions 227 are used to create three-dimensional representations of teeth and/or aligners 231. The intermediate positions 229 are determined in pathway determination step 209. An orthodontic treatment plan that includes the three-dimensional representations of the teeth and/or aligners 231 is determined in step 211. If the orthodontic treatment plan only includes three-dimensional representations of the teeth, these can be used to vacuum-form the aligners onto a 3D printed structure based on the three-dimensional representations of the teeth. Alternatively, for example, the orthodontic treatment plan may comprise a 3D printable file comprising the three-dimensional representations of the aligners, which may then be created using e.g. a 3D printer or other fabrication technologies such as milling, cutting, etc.

Final tooth positions 227 and intermediate tooth positions 229 may be represented as vectors with reference to the centers of gravity of the teeth at the corresponding starting tooth positions as represented in the input data or as 3D representations of teeth at the final tooth positions 227 and/or at the intermediate tooth positions 229, for example. These 3D representations may comprise meshes, voxels or point clouds, for example. Meshes may be converted to point clouds. The three-dimensional representations of the teeth and/or the aligners 231 determined in step 211 are further based on data relating to tooth crowns obtained from a patient intraoral scan 221, which is obtained in step 201. This data relating to tooth crowns obtained from the patient intraoral scan 221 has been preferably automatically spatially aligned (superimposed) with the data obtained from the patient CT scan 223 before it is used in step 211. It has also preferably been automatically segmented into individual teeth crowns and gum tissue surfaces. Patient intraoral scan 221 may be a scan originally produced by an intra oral scanner or a 3D data set derived therefrom, for example.

Figure 3:
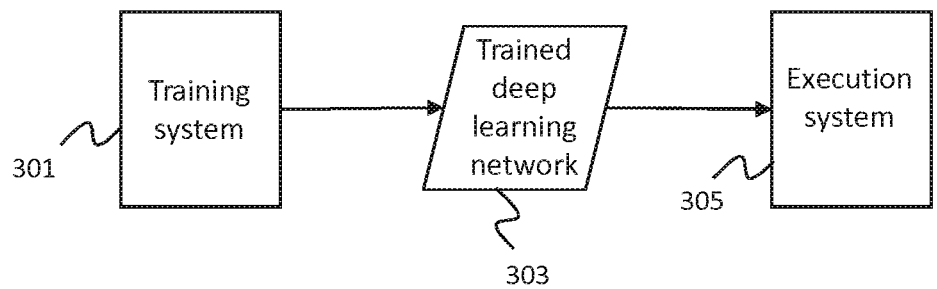
FIG. 3 is a block diagram of a first embodiment of the systems of the invention.

A first embodiment of the systems of the invention is shown in FIG. 3. In this first embodiment, a training system 301 and a separate execution system 305 are present. The training system 301 comprises at least one processor configured to obtain a plurality of training dental computed tomography scans which reflect a moment before respective successful orthodontic treatments, identify individual teeth and jaw bone in each of the training dental computed tomography scans, and train a deep neural network with training input data obtained from the plurality of training dental computed tomography scans and training target data per training dental computed tomography scan to determine a desired final position per tooth from input data obtained from a patient dental computed tomography scan. The training input data obtained from a training dental computed tomography scan represents all teeth and the entire alveolar process and identifies the individual teeth and the jaw bone.

The execution system 305 comprises at least one processor configured to obtain a patient dental computed tomography scan, identify individual teeth and jaw bone in the patient dental computed tomography scan, and use the deep neural network trained on training system 301 to determine a desired final position per tooth from input data obtained from the patient dental computed tomography scan. The input data represents all teeth and the entire alveolar process and identifies the individual teeth and the jaw bone. The determined desired final positions are used to determine a sequence of desired intermediate positions per tooth and the determined intermediate and final positions are used to create three-dimensional representations of aligners. The trained deep neural network is transferred from the training system 301 to the execution (inference) system 305.

Figure 4:
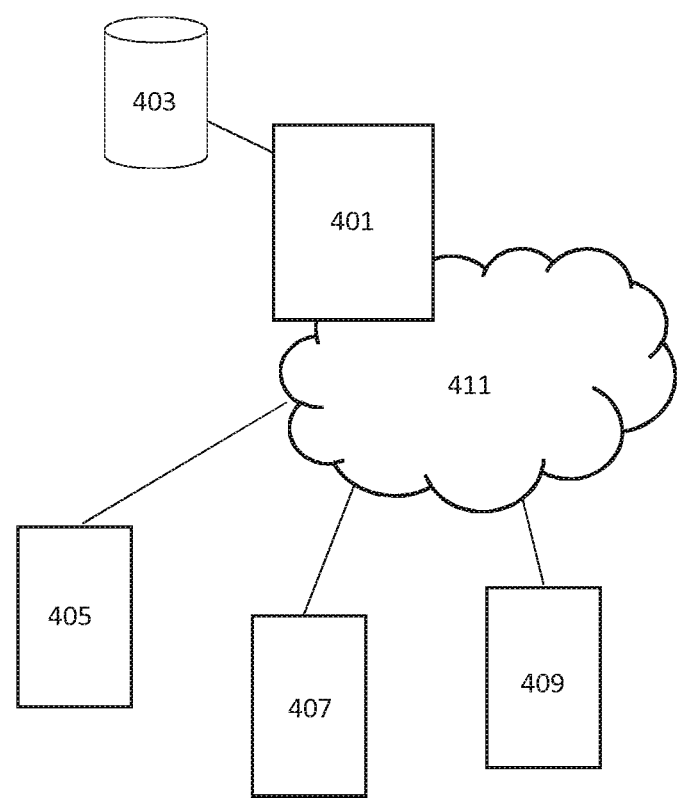
FIG. 4 is a block diagram of a second embodiment of the systems of the invention.

A second embodiment of the systems of the invention is shown in FIG. 4. In this second embodiment the training of the deep neural network and the execution of the deep neural network are performed on the same system, i.e. server 401. The data that forms the deep neural network is stored on storage means 403. Three client devices 405, 407 and 409 communicate with the server 401 via the Internet 411. Each of the three client devices 405-409 may be configured to be able to train the deep neural network, to execute the deep neural network and related software (in order to determine final tooth positions and preferably determine an orthodontic treatment plan), or both. In the embodiment of FIG. 4, three client devices are present. In an alternative embodiment, more or less than three client devices may be present.

Figure 5:
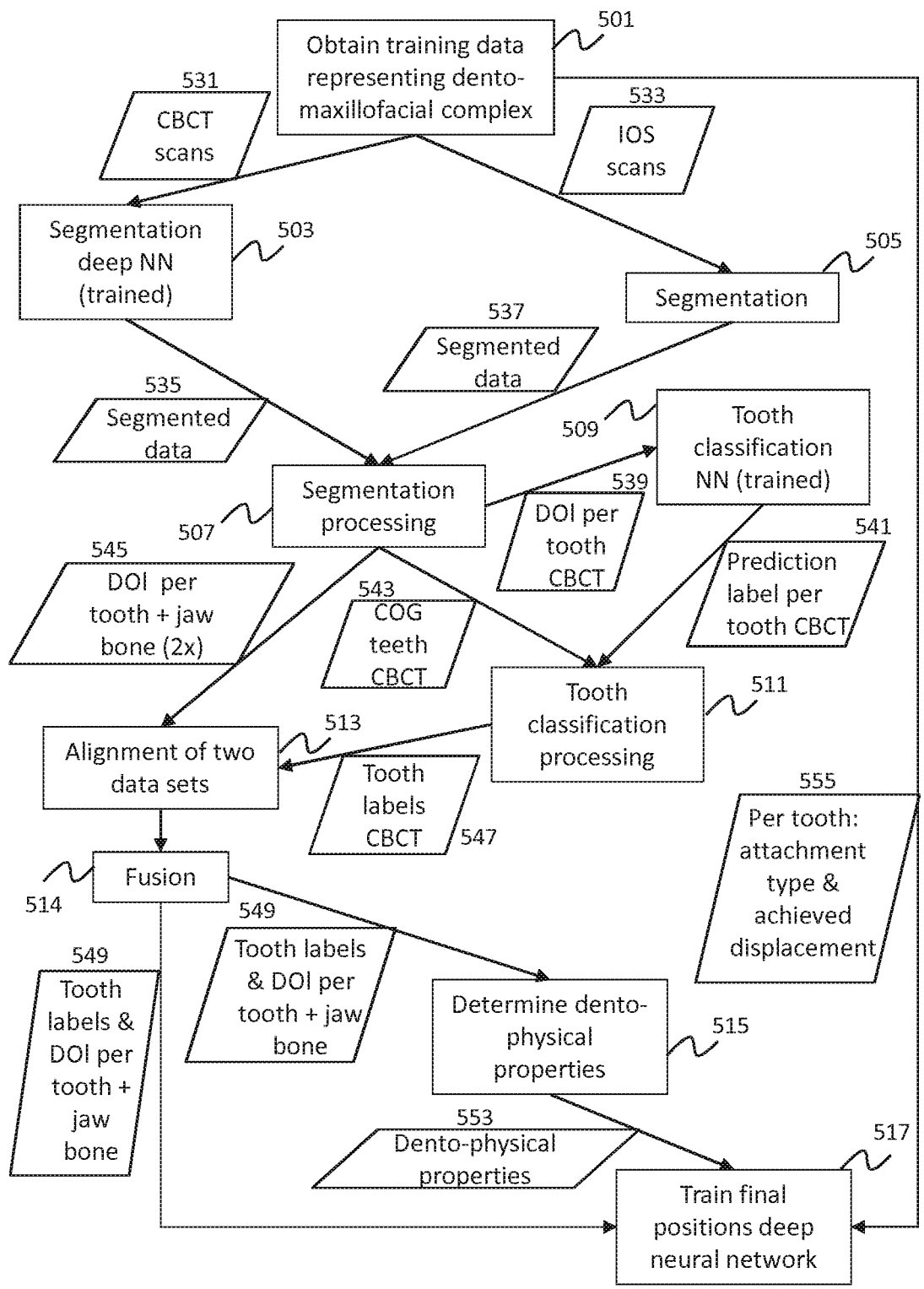
FIG. 5 shows a flow diagram of a second embodiment of the method of training a deep neural network of the invention.

A second embodiment of the method of training a deep neural network of the invention is shown in FIG. 5. Step 501 is somewhat similar to step 101 of FIG. 1, In step 501, training data is obtained. This training data comprises CBCT scans 531 and intraoral scans 533 of already treated patients before their orthodontic treatment. These scans may be the scans as originally produced by a CBCT scanner and intraoral scanner (IOS), respectively, or 3D data sets derived therefrom. The CBCT scans 531 represent the dento-maxillofacial complex of different persons and represent at least the teeth and the entire alveolar process of these persons. The CBCT scans 531 may further represent all basal bone.

The training data further includes data 555, which comprises an indicator indicating an achieved transformation per tooth, e.g. a rotation and/or translation per tooth, and an indicator indicating a used attachment type per tooth. In an alternative embodiment, instead of including an indicator indicating an achieved transformation per tooth, CBCT scans and/or IOS scans from both before and after an orthodontic treatment may be provided as training data to allow the final positions deep neural network to automatically determine the achieved transformation per tooth. The attachment type indicator may indicate one of plurality (e.g. eight) of possible attachment types. (which may each correspond to an 3D model of an attachment). An attachment is e.g. a circular-shaped, rectangular-shaped 3D structure which is used to exercise additional biomechanical pressure on a tooth. By providing the attachment type, it can be correlated to movements implicitly in the final positions deep neural network. Note that an attachment type indication for 'no attachment' may be utilized.

In this embodiment, the CBCT scans 531 are provided to a trained deep neural network for segmentation, which is used in step 503, and the IOS scans 533 are segmented in step 505. This may be performed e.g. by techniques known in the art as described by Wu K et al in "*Tooth segmentation on dental meshes using morphologic skeleton*", Elsevier Computers & Graphics 38 (2014) 199-211, or by a trained neural network. The deep neural network for segmentation is able to segment CBCT scans (e.g. represented by voxels) and the segmented data 535 resulting from step 503 is processed in step 507. The IOS scans, which may be represented by meshes, are segmented in step 505 and the segmented data 537 resulting from this step 505 are processed in step 507 as well, but separately.

Steps 503-507 are somewhat similar to step 103 of FIG. 1, but do not only identify the individual teeth and the jaw bone in the CBCT scans and IOS scans, but also separate them into separate Data of Interest (DOIs). The DOIs determined per tooth from the CBCT scans 531 are provided to a trained tooth classification neural network as data 539. The DOIs determined per tooth from the CBCT scans 531 and from the IOS scans 533 and the DOIs representing the jaw bone determined from the CBCT scans 531 and IOS scans 533 (data 545) are aligned in step 513.

Step 507 also involves determining Centers of Gravity (COGs) 543 per tooth from the segmented data 535 (obtained from the CBCT scans 531). These COGs are used in step 511 along with a prediction 541 for a label per tooth received from the tooth classification neural network. The tooth classification neural network has determined this prediction 541 in step 509 based on the data 539. Step 511 involves processing the tooth classification, i.e. the prediction 541, in part making use of the COGs 543. The resulting tooth labels 547 are used to align the data sets obtained from the CBCT scans 531 with the data sets obtained from the IOS scans 533. Steps 507-511 are performed for each CBCT scan. The data sets are then fused in step 514, e.g. by methods as described by Hong-Tzong Yau et al in "*Tooth model reconstruction based upon data fusion for orthodontic treatment simulation*", Elsevier Computers in Biology and Medicine 48 (2014) 8-16. Data 549 comprising the fusion of these data sets plus the tooth labels determined in step 511 are used in steps 515 and 517.

In step 515, the fused DOI per tooth and the DOI for jaw bone (i.e. data 549) are used to determine the dento-physical properties 553 for each of the training dental computed tomography scans 531 and these dento-physical properties 553 are encoded in the final positions deep neural network in step 517. The dento-physical properties 553 may comprise the physical conditions and restraints of the teeth and the bony housing (the dento-alveolar complex), for example. In step 517, the final (tooth) positions deep neural network is trained using training data which includes, for each pair of CBCT scan and IOS scan, data 549 (tooth labels, fused DOI per tooth and DOI for jaw bone), dento-physical properties 553 and data 555 (indicator indicating an achieved transformation per tooth, which is a vector in this embodiment, and indicator indicating a used attachment type per tooth). Step 517 is somewhat similar to step 105 of FIG. 1.

During such training, a loss function may be employed as a measure to be minimized. This optimization effort may be aided by making use of optimizers such as SGD, Adam, etc. A loss function calculates an error between the desired output (being training targets) and the predicted output (at the specific moment in time during training). The internal parameters of the neural network are adjusted as to minimize this error. Various well know loss functions exist, each being more or less suitable for different problems (e.g. categorical cross-entropy for classification, mean absolute or squared error for regression, Dice loss for segmentation, etc.).

Various aspects of the model and its training are influenced by the choice of loss function, such as the potential duration of training to reach a desired accuracy, requirements to the variety of training samples, the potential achievable accuracy, etc.

In the context of a final position deep neural network, a specific loss function may be utilized during training. Whilst the neural network may e.g. be optimized using a mean squared error loss based on the predicted and desired vectors in the case of an embodiment, a loss function more specific for this problem may make use of dento-physical properties that may be determined based upon the input data and/or may be known to be universally applicable.

Whilst e.g. making use of a mean squared error loss function does not exclude derivation of relevant information considering dento-physical properties from being encoded within the internal parameters of the neural network (as long as these can potentially be derived from the input data as supplied), such custom loss function may create a more applicable total measure of error. By e.g. (proportionally) employing a component of error measuring the amount of difference between a desired amount of surface contact between teeth and jaw, and/or an appropriate increase of error in cases were teeth may be placed outside of the bony housing, and/or an appropriate increase in error where teeth may have overlap between their respective volumes, etc., the neural network may be more specifically trained to derive relevant information considering these properties, effectively encoding this derivation as specific as may be possible given the information in the input data.

Figure 6:
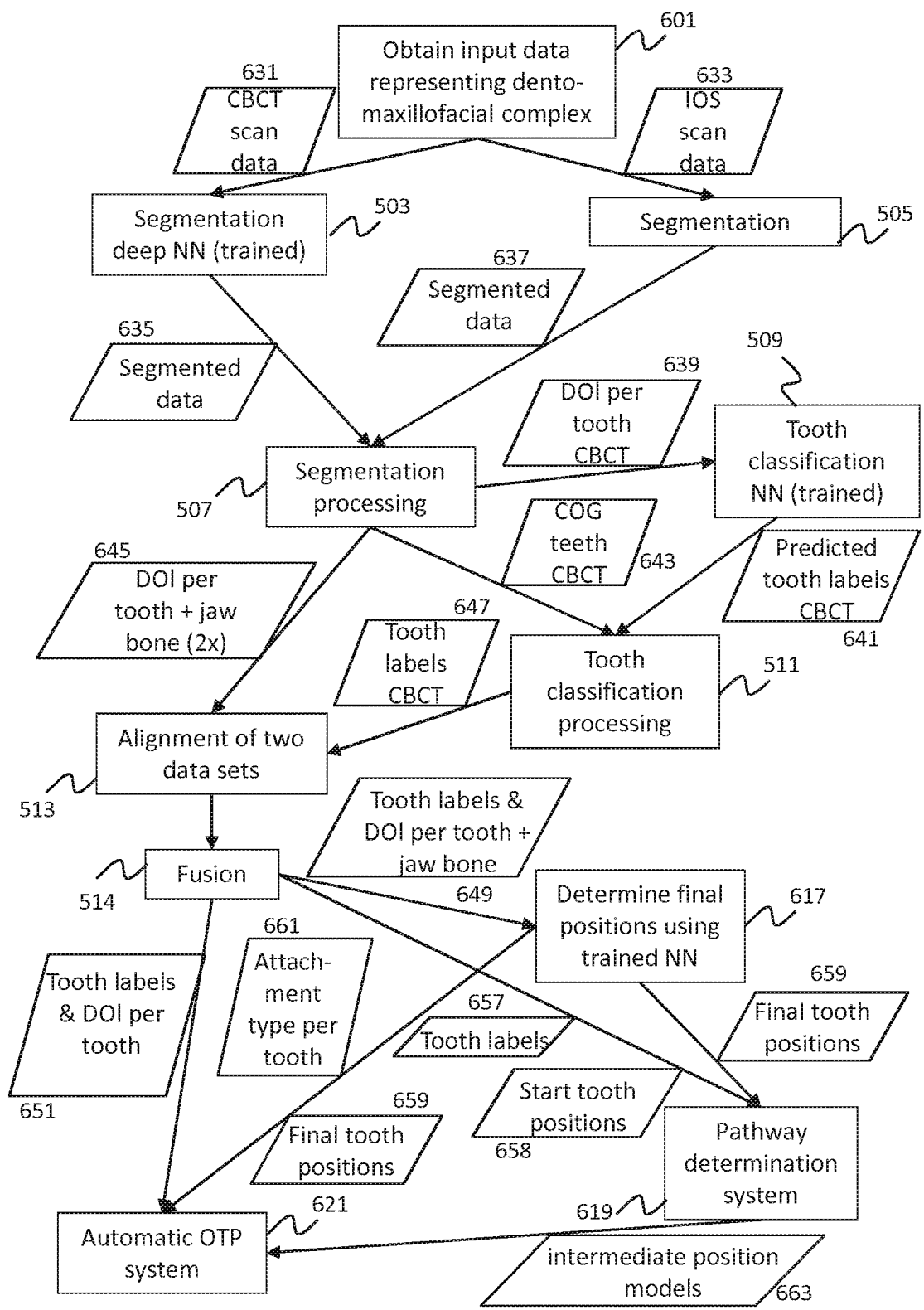
FIG. 6 shows a flow diagram of a second embodiment of the method of determining an orthodontic treatment plan of the invention.

A second embodiment of the method of determining an orthodontic treatment plan is shown in FIG. 6. Step 601 is somewhat similar to steps 201 and 203 of FIG. 2.

In step 601, input data is obtained. This input data relates to a patient with malocclusion in need of orthodontic treatment and comprises a CBCT scan 631 and an intraoral scan 633. These scans may be the original scans as produced by a CBCT scanner and intraoral scanner (IOS), respectively, or 3D data sets derived therefrom. The CBCT scan 631 represents the dento-maxillofacial complex of a patient and represents at least the teeth and the entire alveolar process of this patient. The CBCT scan 631 may further represent all basal bone.

The same steps 503 to 514 performed in the method of FIG. 5 are also performed in the method of FIG. 6, but now for input data (relating to a patient still to be treated) instead of for training data (of a plurality of persons who have already been treated). This difference is also reflected in data 631-649, which is similar to data 531-549 of FIG. 5. Steps 503-507 are somewhat similar to step 205 of FIG. 2.

Three new steps are present in the method of FIG. 6. Step 617 comprises determining final tooth positions using the deep neural network trained with the method of FIG. 5. Step 619 comprises determining pathways, i.e. intermediate tooth positions 663. Step 621 comprises determining an orthodontic treatment plan. Step 617 is somewhat similar to step 207 of FIG. 2. Step 619 is somewhat similar to step 209 of FIG. 2. Step 619 is somewhat similar to step 211 of FIG. 2.

In step 617, the final tooth positions are determined based on data 649, which includes tooth labels, a fused DoI per tooth and a fused DoI for the jaw bone.

Performing step 617 results in final tooth positions 659 and an attachment type per tooth 661. The final tooth positions 659, e.g. transformation vectors with reference to the COGs of the teeth at their starting positions as reflected in the DOIs, are used in step 619. In step 619, the final tooth positions 659 are used along with the tooth labels 657 and the start tooth positions 658 to determine the intermediate tooth positions 663 (which are in this embodiment 3D models, e.g. meshes). The tooth labels 657 and the start tooth positions 658 are related to on the fused data sets to ensure that a start tooth position, a final tooth position and a tooth label refer to the same tooth/DOI. The intermediate tooth positions 663 are used in step 621.

Step 621 comprises automatically determining an orthodontic treatment plan, including 3D models of aligners or 3D structures to create such aligners. The orthodontic treatment plan is determined based on the data 651, final tooth positions 659, the attachment type per tooth 661 and the intermediate tooth positions 663. Data 651 is the same as data 649, but without the DOI for the jaw bone.

Figure 7:
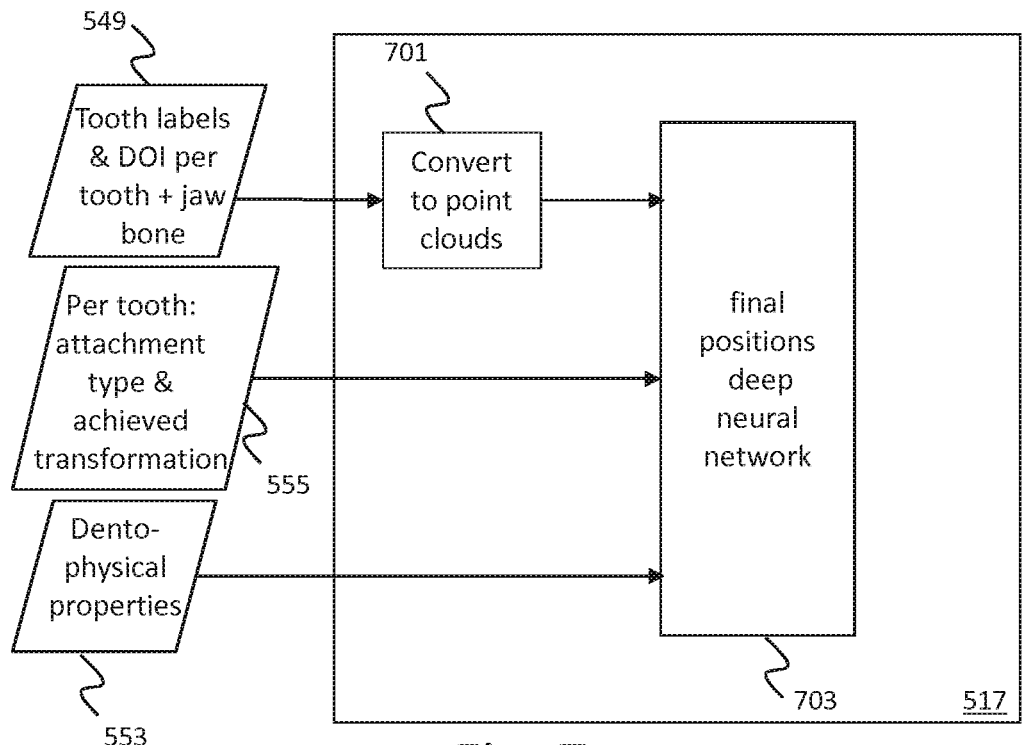
FIG. 7 shows an embodiment of the step of training the final positions deep neural network of FIG. 5.

FIG. 7 shows an embodiment of step 517 of FIG. 5. Step 517 comprises training a final (tooth) position deep neural network 703. The data used in step 517 comprises data 549, data 555 and dento-physical properties 553, as depicted in FIG. 5 The data 555, which comprises a used attachment type per tooth and an achieved transformation per tooth, and the dento-physical properties 553 are included in the training data for the deep neural network 703. The data 549 comprises a DOI per tooth and a DOI for the jaw bone.

If data 549 comprises a voxel representation, this voxel representation may be converted to surface meshes (e.g. by means of a marching cubes algorithm and post-processing such as 3D mesh smoothing), and subsequently converted to (a) point cloud(s) in step 701 (e.g. by creating a representative 3D point per defined face, at the position of the average points defining such a face).

Surface mesh data formats inherently describe a delineating surface of a volume in 3D and, as such, do not store any data from within such volume. Furthermore, compared to e.g. voxel representations, data points as described do not need to be placed upon e.g. a pre-determined grid of a pre-determined resolution. This makes a surface mesh format more accurate for describing structures e.g. given the same amount of stored data. This accuracy is beneficial for solving the problem of determining final tooth positions. Faces as described in surface mesh data may accurately be represented by (a) point cloud(s), e.g. by generating an appropriate 3D point per applicable face. Such a conversion to point cloud(s) removes redundancy in the surface mesh definition and makes the 3D data more applicable for processing by certain types of deep neural network.

The training data 549 and 555 may be sourced from existing treatment results or plans. Alternatively, training data 549 and 555 may be generated from data representing a dentition not having malocclusion. A system component may manipulate this received data in such a way that malocclusion is simulated by displacing the individual teeth randomly, be it within feasible boundary conditions. Such boundary condition may consider collisions, maximum possible transformations, etc. Additionally, appropriate attachments and dento-physical properties may be generated. The randomly generated transformation represent the target transformations to be predicted by the final tooth positions deep neural network. Such component would effectively generate a vast majority of samples to be utilized during training of the network.

Figure 8:
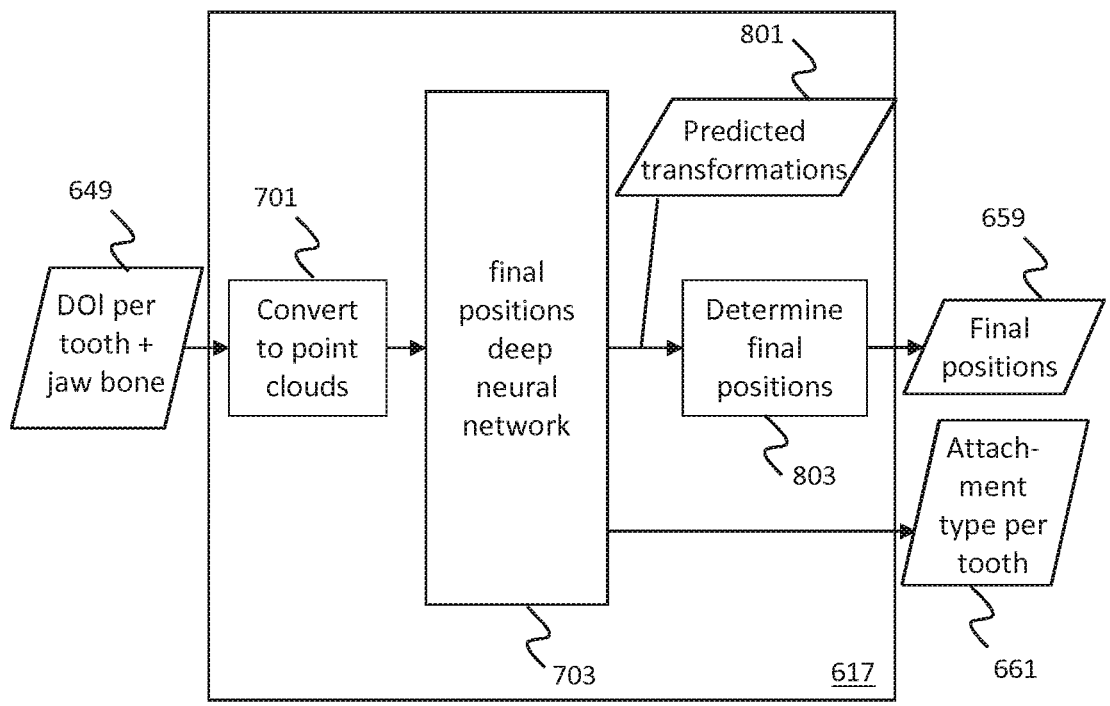
FIG. 8 shows an embodiment of the step of determining final tooth positions of FIG. 6.

FIG. 8 shows an embodiment of step 617 of FIG. 6. The data used in step 617 comprises data 649, as depicted in FIG. 6. The data 649 comprises DOIs per tooth and a DOI for the jaw bone represented as meshes and tooth labels. These meshes are first converted to point clouds in step 701 and then included in the input data for the deep neural network 703. The execution of the deep neural network 703 results in an output of predicted (tooth) transformation 801. This predicted transformation 801 is used to determine final (tooth) positions 659 in step 803. The execution of the deep neural network 703 further results in an output of an attachment type per tooth 661.

Outputs as resulting from the embodiment as described with respect to FIG. 8 may be used as a measure (or score) in non-automatic systems for the determination of orthodontic treatment planning. Such a score may serve as feedback where a clinician might prefer determining final positions manually instead of fully automatically. Feedback may be given to a clinician performing manual positioning of teeth of a dentition within e.g. a software package for orthodontic treatment planning. Given any moment in time during such manual positioning, appropriate input may be generated to be fed into the neural network and predicted transformation and/or attachment types per tooth may be used to calculate a general score of 'correctness' of occlusion of the entire dentition and/or a score of 'correctness' of placement/attachment per individual tooth. Alternatively, the network may be utilized to generate final positions once, from the input situation as may be received by such software package, and differences between the situation being manually positioned and the single predicted final positions may be calculated for generating such scores. In an alternative embodiment, the neural network 703 outputs a score directly.

Figure 9:
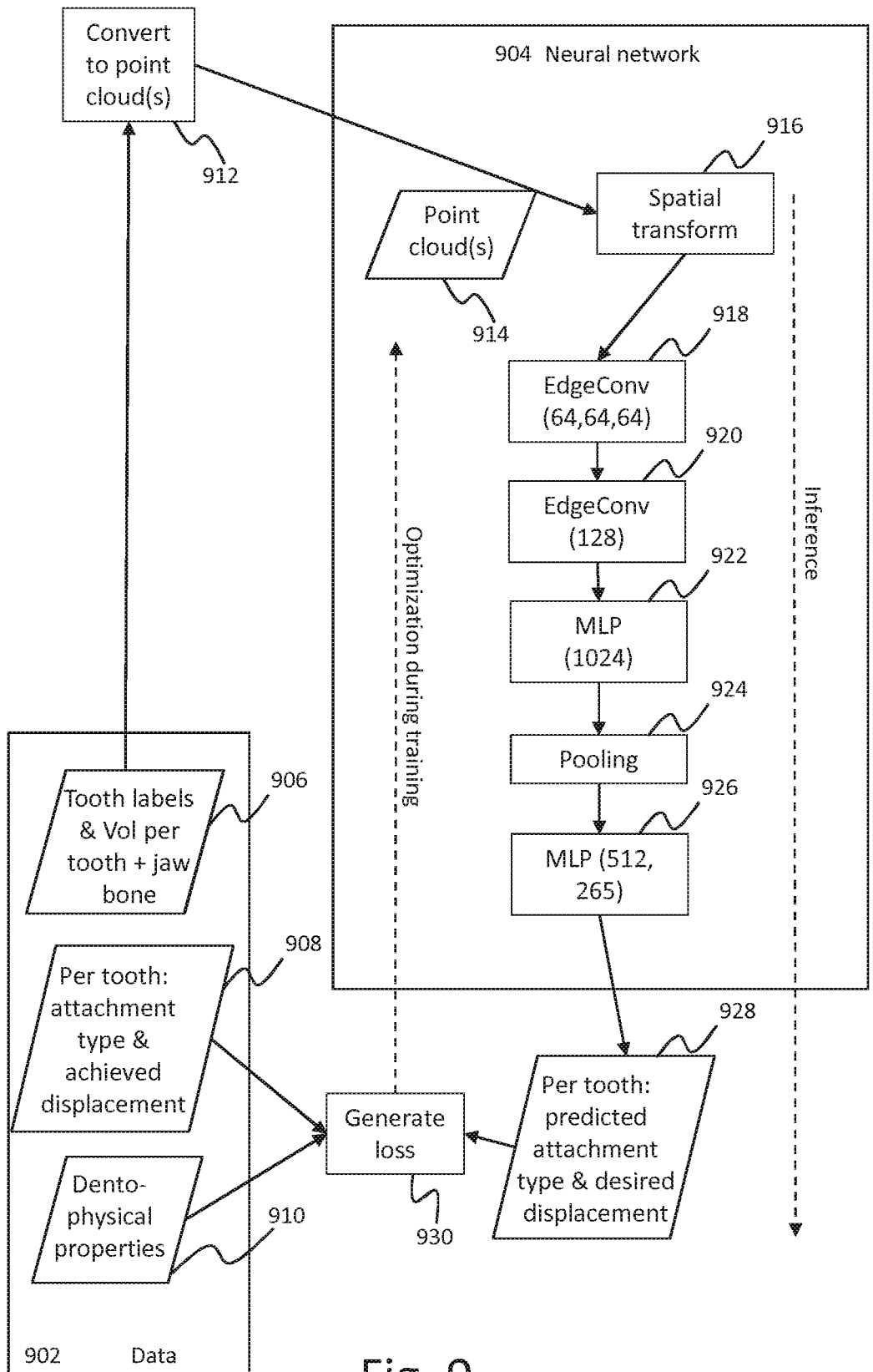
FIG. 9 shows an embodiment of the architecture of a deep neural network for determining final tooth positions of FIGS. 7 and 8.

FIG. 9 depicts an exemplary final positions deep neural network. Due to the benefits of working on 3D point cloud data, network architectures appropriate for processing such an input may be utilized. Architecture types known to be appropriate include PointNets and improvements upon these such as PointNet++, geometric deep learning approaches such as graph convolutional neural networks, and more recently dynamic graph convolutional neural networks and fully-convolutional point networks. Components of such architectures in part overlap and in part differ, with the differing parts mostly applying to to the extent of spatial context that may be processed for encoding information relevant to the problem to be solved. Such network architectures are commonly employed for performing 3D point cloud classification, segmentation and/or part segmentation. Regression problems are exemplified to be solvable by such architectures as well.

In an embodiment, training targets (hence values to be predicted) for such a final positions neural network may consist of numerical values representing a transformation per tooth. Such values may represent translations and rotations as required to counter malocclusion as might be present in the input data. An additional set of training targets may be a classification of an attachment type to be used per tooth. Such classification may include a class representing 'no attachment'.

Input data may consist of a cloud of points, being defined in at least 3 dimensions, these 3 dimensions representing coordinates in 3D space. Additional dimensions may be included, e.g. a fourth dimension encoding a value representing which part of a structure as identified a point belongs to. In an alternative embodiment, 3D point clouds per identified structure are offered to the input of the final position 3D deep neural network as separate inputs.

In an alternative embodiment, e.g. in cases where available computational aspects such as processing power, available memory, etc., are limited, data for both training and inference might be pre-selected to focus on just one tooth and its surrounding spatial context. Giving a large enough supplied context, desired transformation and/or attachment types may in such a manner be generated per individual tooth, effectively training an 'individual tooth final position neural network'. Whilst it might be expected that desired occlusion (alignment) of both dental arches is a problem requiring all spatial context as input, given a large enough set of training samples, a generalization may be achieved that, though requiring to perform inference per individual tooth, would resolve correct occlusion of both complete arches.

In the exemplary embodiment of FIG. 9, data 902 comprises data 906, 908 and 910, where 906 is utilized for performing inference employing a trained neural network 904, and matching sets of 906, 908 and 910 may be required for training neural network 904. Prediction is performed on point cloud(s) 914 which are derived at step 912. Predictions 928 may consist of desired transformations and attachment types per tooth. Data 906 corresponds to data 549 of FIG. 5 when used for training and to data 649 of FIG. 6 when used for inference. Dento-physical properties 910 correspond to dento-physical properties 553 of FIG. 5. The neural network 904 corresponds to the neural network 703 of FIGS. 7 and 8.

Optimization of the internal parameters of the neural network may be achieved utilizing a loss function 930 taking into account the actual to be predicted transformations and attachment types 908 and dento-physical properties 910 and predictions 928. Note that 'no attachment' may be a class of attachment.

Such a neural network may employ a component performing a spatial transform 916 in the input data as may be found in PointNets. This spatial transform is utilized to make ensure invariance against the ordering of the point cloud as presented (permutation invariance).

EdgeConv components 918, 920 as proposed by Wang et al. in "Dynamic graph CNN for learning on point cloud" (arXiv:1801.07829 [cs.CV]) have the potential of capturing local geometric features. Such components perform graph-based operations to derive useful information, and a dynamic graph update results in a differing graph definition per added EdgeConv layer. A max pooling component 922 and consecutive pooling 924 over subsets of points being processed may be employed to aggregate a global set of relevant features, followed by a multi-layer perceptron (MLP) component 926 aimed to encode further required logic for generating predictions 930.

Alternatively, such a neural network may utilize one or more χ-Conv operators as proposed by Li et al. in "PointCNN: Convolution On χ-Transformed Points", published in NIPS'18 Proceedings of the 32nd International Conference on Neural Information Processing Systems, pages 828-838, and such a neural network may thus utilize χ-transformed features Methods and systems for segmentation of point cloud data (IOS data in particular) are also described in European patent application no. 18213246.4 with title "Automated semantic segmentation of non-Euclidean 3D data sets using deep learning" and European patent application no. 19186357.0 with title "Object detection and instance segmentation of 3D point clouds based on deep learning", which are hereby incorporated by reference in this application.

It should be noted that this is just an exemplary embodiment and amounts of layers, ordering of such layers, amounts of nodes/filters, etc. may vary. Described components may consist of sub-components which are known in the art such as max pooling layers, convolutional layers, concatenation layers, etc.

Figure 10:
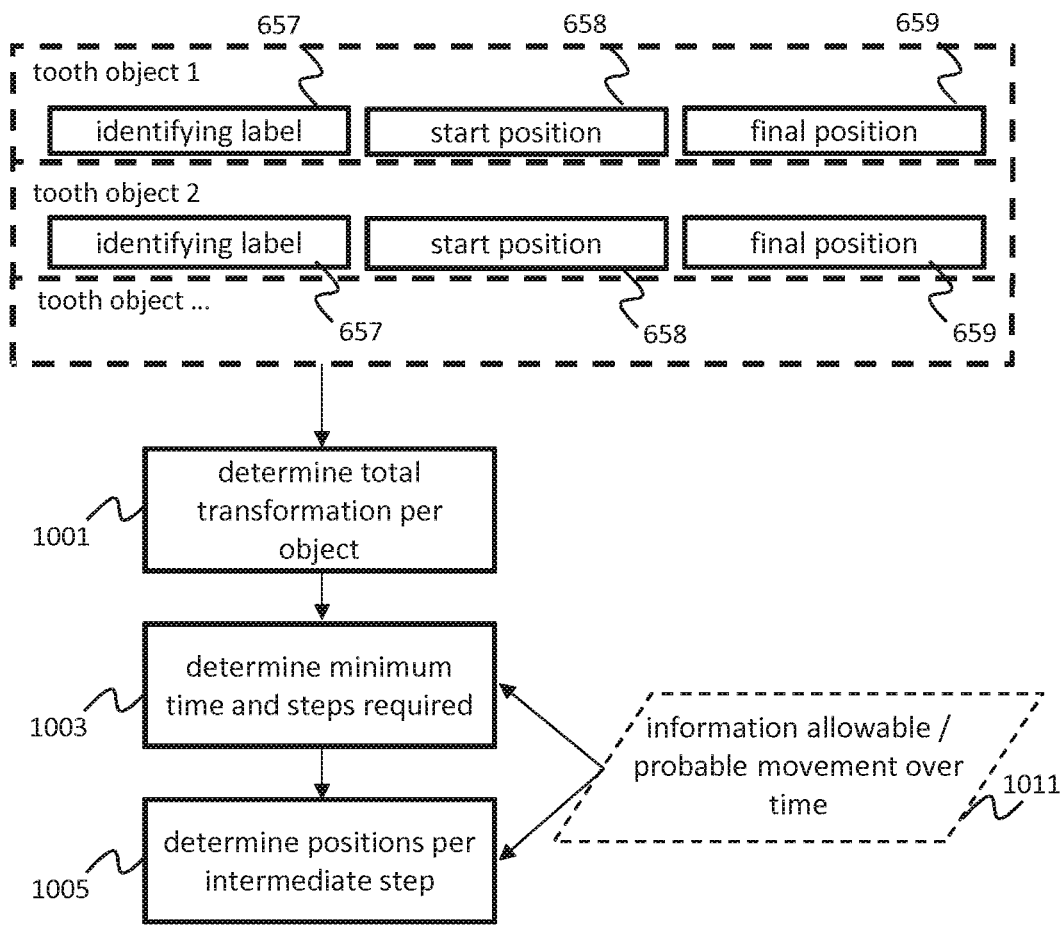
FIG. 10 shows an embodiment of the pathway determination step of FIG. 6.

FIG. 10 shows an embodiment of step 619 (pathway determination) of FIG. 6. Tooth labels 657, start (tooth) positions 658 and final (tooth) positions 659 are used in this step 619. Step 619 comprises sub steps 1001, 1003, and 1005. Step 1001 comprises determining a total transformation per object (tooth). Step 1003 comprises determining a minimum time and steps required for this total transformation. Step 1005 comprises determining positions per intermediate step. Information 1011 on allowable and/or probable movement is used in these steps 1003 and 1005.

Figure 11:
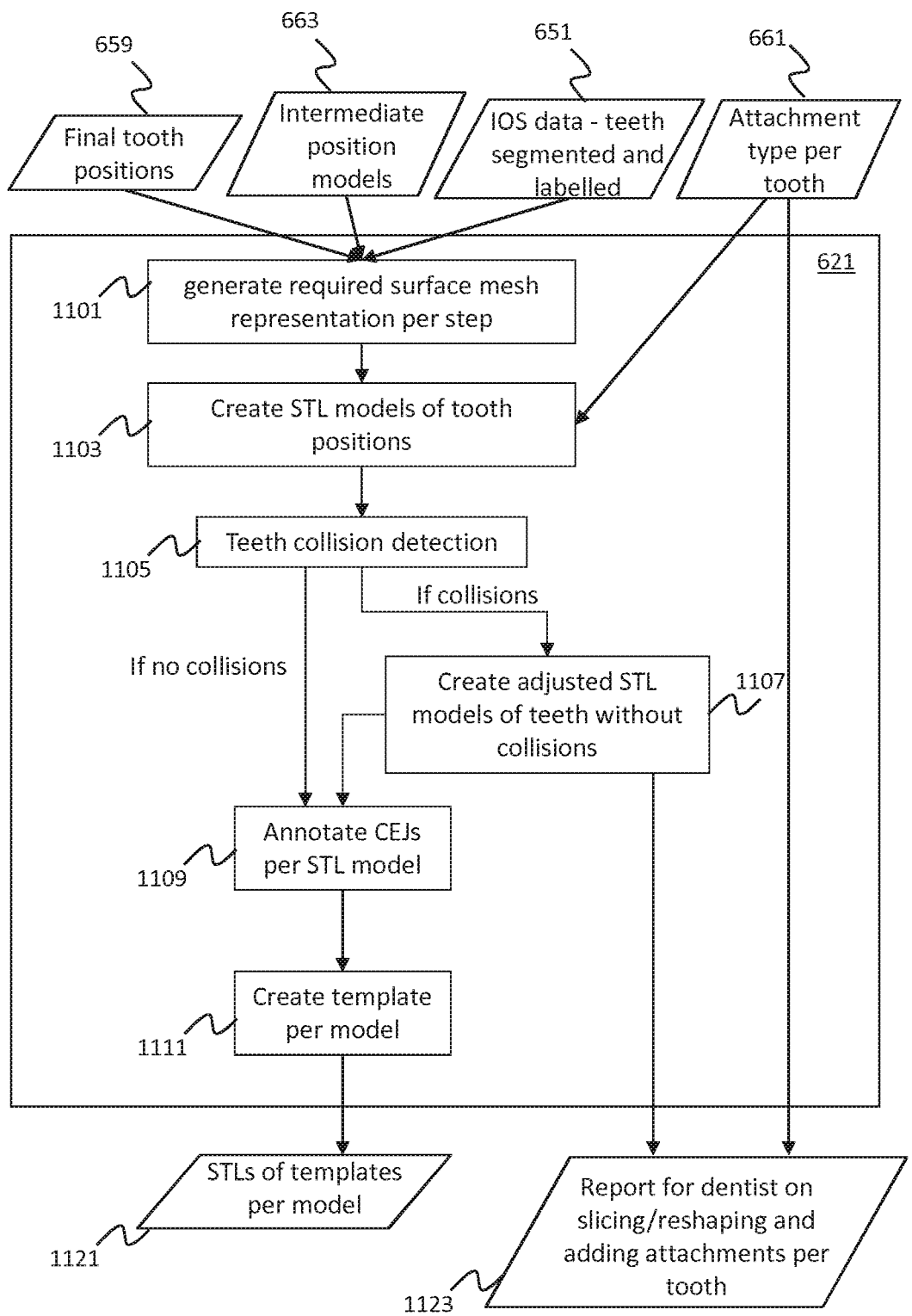
FIG. 11 shows an embodiment of the automatic orthodontic treatment planning step of FIG. 6.

FIG. 11 shows an embodiment of step 621 (orthodontic treatment planning) of FIG. 6. Final tooth positions 659, intermediate positions 663, data 651 and attachment type per tooth 661 are used in this step 621. Data 651 typically includes IOS data in which the teeth have been segmented and labelled. The tooth labels may be numbers conforming to a certain numbering system, e.g. the Universal Numbering System, FDI notation, text labels, e.g. "(R) Cuspid", or different types of labels. Important is that the same tooth labels are used in each applicable step. The label may e.g. be encoded in the names of the files comprising the teeth data sets or e.g. b e related to the applicable data by including metadata. In this embodiment, data 649 is a fusion of a pair of CBCT and IOS scans. Step 621 comprises sub steps 1101-1111.

In the embodiment of FIG. 11, the final tooth positions 659 and the intermediate positions 663 are represented by vectors, Step 1101 comprises generating a surface mesh representation per step (position) from the final tooth positions 659, the intermediate positions 663 and the data 649. These surface meshes are used in step 1103 along with the attachment type per tooth 661 to create 3D models for each of the intermediate and final tooth positions, each 3D model representing all teeth. In step 1105, teeth collision detection is performed between teeth in the same 3D model. If collisions are detected, a step 1107 is performed. Step 1107 comprises creating one or more adjusted 3D models of teeth without collisions. Step 1109 is performed after step 1107. Step 1109 is performed directly after step 1105 if no collisions are detected.

Step 1109 comprises annotating the Cemento Enamal Junctions (CEJs) per 3D model. Annotation of the CEJs may be performed, e.g. by techniques known in the art as described by Wu K et al in "*Tooth segmentation on dental meshes using morphologic skeleton*", Elsevier Computers & Graphics 38 (2014) 199-211, (identifying the delineation between tooth and gum, but omitting delineation between tooth crowns), or by a trained neural network. Utilizing this annotation, effectively boundaries of a 3D volume are defined, delineating boundaries for a to be generated aligner.

Step 1111 comprises creating a template for an aligner per 3D model by e.g. utilizing the inverse of the represented volumes. The result of step 1111 is a sequence of 3D models of aligner templates 1121, one for each 3D model of the tooth positions (visualized in 1201). In this embodiment, the orthodontic treatment plan further comprises a report 1123 for the dentist on slicing/reshaping and adding attachments per type. This report 1123 includes the determined attachment type per tooth 661 and information on the adjustments performed in step 1107.

Figure 12:
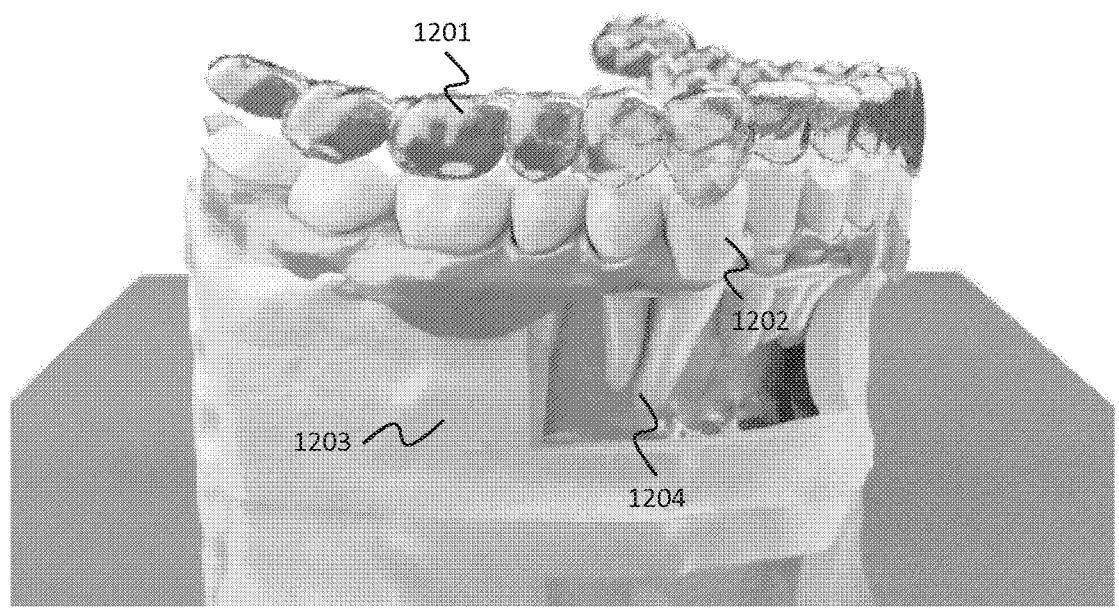
FIG. 12 shows a computer render (rendering) visualizing the resulting outcome of automated aligner design for a specific case according to various embodiments of the invention.

FIG. 12 shows a computer render (rendering) visualizing the resulting outcome of automated aligner design for a specific case according to various embodiments of the invention. The 3D surfaces visualized as 1202 and 1204 comprise the same tooth and are derived from both CBCT and IOS image data. It can be seen that the spatial accuracy of the IOS data (crown part) is higher than that of the CBCT derived data (root part). It can also be seen that the teeth have been placed in their desired positions with respect to the dento-physical properties of the dento-alveolar process 1203, in the case of this visualization the desired positions for step one in the sequence of consecutive steps. For this single step an aligner 1201 has been generated.

Figure 13:
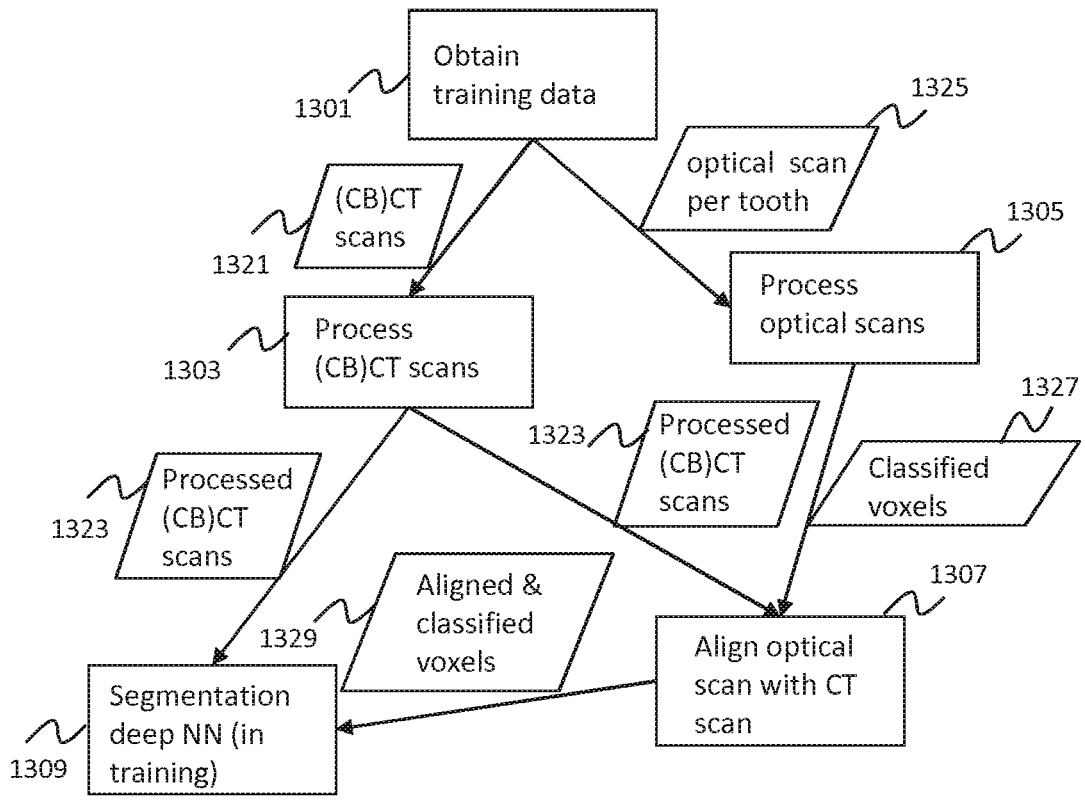
FIG. 13 shows a flow diagram of an embodiment of a method of training the segmentation deep neural network of FIGS. 5 and 6.

FIG. 13 shows a flow diagram of an of a method of training the segmentation deep neural network of FIGS. 5 and 6. In step 1301, CBCT 3D image data 1321 of a dento-maxillofacial structure is obtained. The structure may include e.g. jaw-, teeth- and nerve structures. The 3D image data 1321 may comprise voxels, i.e. 3D space elements associated with a voxel value, e.g. a greyscale value or a color value, representing a radiation intensity or density value. The CBCT 3D image data 1321 may conform to the DICOM format or a derivative thereof, for example. In step 1303, the CB(CT) 3D image data is processed before it is fed to the input of the segmentation deep neural network 1309. Such processing may comprise normalizing voxel values to a range that is more beneficial for a neural network, for example.

In order to make the segmentation deep neural network 1309 robust against the variability present in e.g. current-day CBCT scan data, the segmentation deep neural network 1309 is trained using optical scans per tooth 1325, which may be represented as 3D models, e.g. meshes. These optical scans may be obtained using a 3D optical scanner. Such optical 3D scanners are known in the art and can be used to produce high-quality 3D jaw and tooth surface data. The 3D surface data may include 3D surface meshes which may be filled (determining which specific voxels are part of the volume encompassed by the mesh) and used by a voxel classifier in step 1305. This way, the voxel classifier is able to generate highly accurate classified voxels 1327 for training. In this embodiment, these classified voxels 1327 are aligned with the processed CBCT 3D image data 1323 in step 1307. The processed CBCT 3D image data 1323 and the aligned and classified voxels 1329 are provided to the segmentation deep neural network 1309 as training data.

In an alternative embodiment, conventional 3D training data is obtained by manually segmenting the CBCT 3D image data, which may represent a significant amount of work. Additionally, manual segmentation results in a low reproducibility and consistency of input data to be used. However, in a variant on the embodiment of FIG. 13, such manually segmented training may additionally be used.

Methods and systems for automatic segmentation based on deep learning are also described in European patent application no. 17179185.8 and PCT application no. PCT/EP2018/067850 with title Classification and 3D modelling of 3D dento-maxillofacial structures using deep learning methods, which is hereby incorporated by reference in this application.

Figure 14:
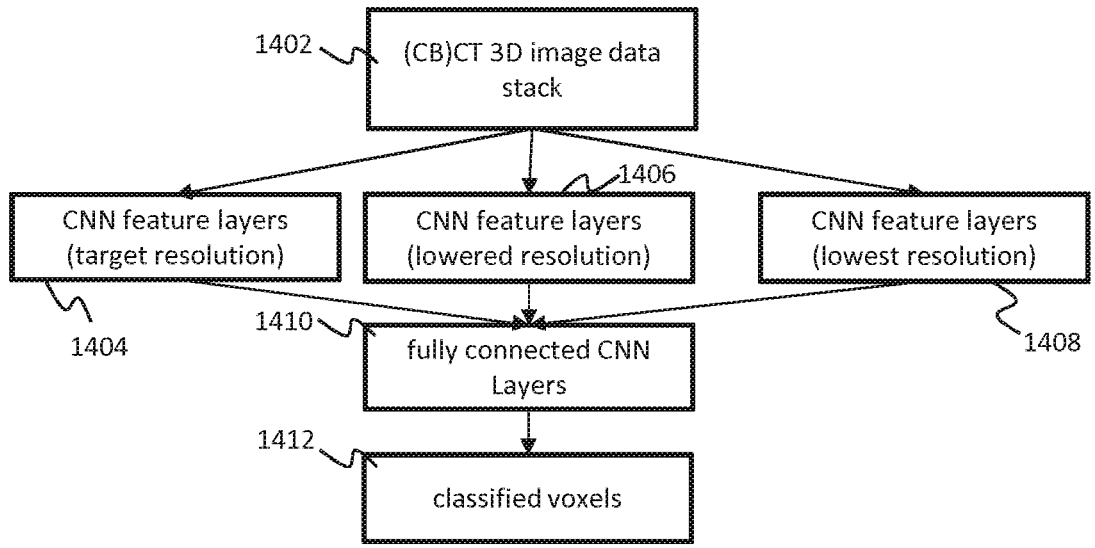
FIGS. 14 and 15 depict examples of a 3D deep neural network architecture for the segmentation deep neural network of FIGS. 5 and 6.
Figure 15:
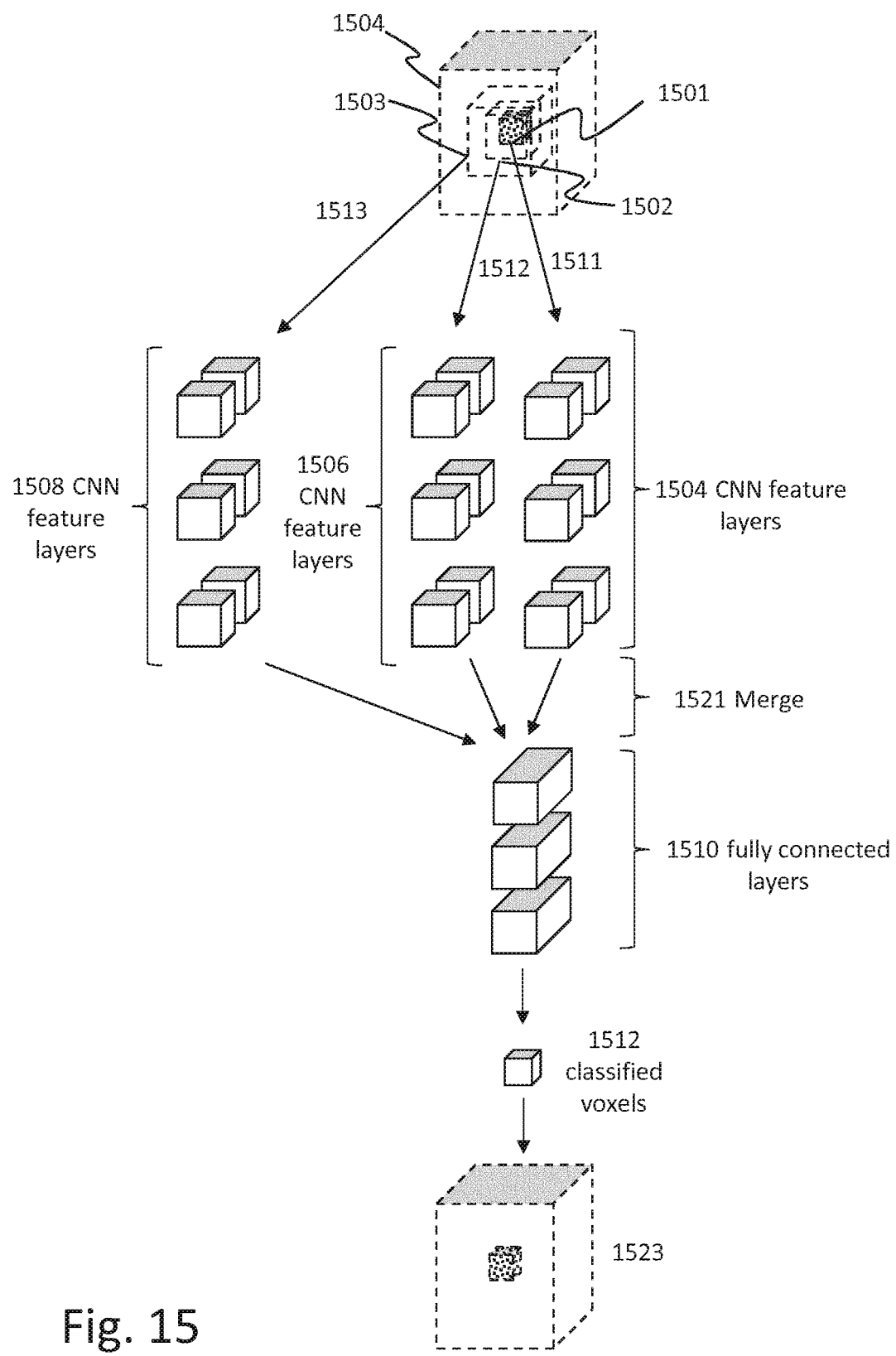

FIGS. 14 and 15 depict examples of a 3D deep neural network architecture for the segmentation deep neural network of FIGS. 5 and 6. As shown in FIG. 14, the network may be implemented using 3D convolutional neural networks (3D CNNs). The convolutional layers may employ an activation function associated with the neurons in the layers such as a sigmoid function, tanh function, relu function, softmax function, etc. A plurality of 3D convolutional layers may be used wherein minor variations in the number of layers and their defining parameters, e.g. differing activation functions, kernel amounts and sizes, and additional functional layers such as dropout layers and/or batch normalization may be used in the implementation without losing the essence of the design of the 3D deep neural network.

The network may include a plurality of convolutional paths, in this example three convolutional paths, a first convolutional path associated with a first set of 3D convolutional layers 1404, a second convolutional path associated with a second set of 3D convolutional layers 1406 and a third set of 3D convolutional layers 1408. A computer executing the data processing may provide a 3D data set 1402, e.g. CT image data, to the inputs of the convolutional paths. The 3D data set may be a voxel representation of a 3D dental structure.

The function of the different paths is illustrated in more detail in FIG. 15. As shown in this figure, voxels of the voxel representation may be provided to the input of the 3D deep neural network. The voxels of the voxel representation may define a predetermined volume, which may be referred to as the image volume 1523. The computer may divide the image volume in first blocks of voxels and provide a first block to the input of the first path. The 3D convolutional layers of the first path 1511 may perform a 3D convolution operation on the first block of voxels 1501. During the processing, the output of one 3D convolution layer of the first path is the input of a subsequent 3D convolution layer in the first path. This way, each 3D convolutional layer may generate a 3D feature representing information considering the first block of voxels that is provided to the input of the first path. A 3D convolutional layer that is configured to generate such features may therefore be referred to as a 3D CNN feature layer.

As shown in FIG. 15, the convolutional layers of the second path 1512 may be configured to process second blocks of voxels 1502 of the voxel representation, wherein a second block of voxels represents a down-sampled version of an associated first block of voxels and wherein the first and second block of voxels have the same centered origin. The represented volume of the second block is larger than the volume of the first block. Moreover, the second block of voxels represents a down-sampled version of an associated first block of voxels. The down-sampling factor may be any appropriate value. In an embodiment, the down-sampling factor may be selected between 20 and 2, preferably between 5 and 3.

The first path 1511 may define a first set of 3D CNN feature layers (e.g. 5-20 layers), which are configured to process input data (e.g. first blocks of voxels at predetermined positions in the image volume) at the voxel resolution of the target (i.e.

voxels of the image volume that are classified). The second path may define a second set of 3D CNN feature layers (5-20 layers), which are configured to process second blocks of voxels wherein each block of the second blocks of voxels 1512 has the same center point as its associated block from the first block of voxels 1511. Moreover, the voxels of the second blocks are processed at a resolution that is lower than the resolution of 1511. Hence, the second blocks of voxels represent a larger volume in real-world dimensions than the first blocks. This way, the second set of 3D CNN feature layers process voxels, generating 3D features that include information about the direct neighborhood of associated voxels as processed by the first 3D CNN feature layers. This way, the second path enables the 3D deep neural network to determine contextual information, i.e. information about the context (e.g. its surroundings) of voxels of the 3D image data as processed by the first set of 3D CNN feature layers.

In a similar way, a third path 1513 may be utilized, to determine further contextual information of first blocks of voxels 1503. Hence, the third path may comprise a third set of 3D CNN feature layers (5-20 layers), which are configured to process third blocks of voxels wherein each block of the third blocks of voxels 1503 has the same center point as its associated block from the first block of voxels 1501 and the second block of voxels 1503. Moreover, the voxels of the third blocks are processed at a resolution that is lower than the resolution of the first and second blocks of voxels. This down-sampling factor may again be set at an appropriate value. In an embodiment, the down-sampling factor may be selected between 20 and 3, preferably between 16 and 9.

By using three paths or more paths, both the 3D image data on the received resolution (the input data) and the additional contextual information about voxels of the 3D image data can be processed in parallel. The contextual information is important for classifying dento-maxillofacial structures, which typically include closely packed dental structures that are difficult to distinguish.

The output of the sets of 3D CNN feature layers are then merged in step 1521 and fed to the input of a set of fully connected 3D CNN layers 1510, which are trained to derive the intended classification of voxels 1512 that are offered at the input of the neural network and processed by the 3D CNN feature layers.

The sets of 3D CNN feature layers may be trained (through their learnable parameters) to derive and pass on the optimally useful information that can be determined from their specific input, the fully connected layers encode parameters that will determine the way the information from the three previous paths should be combined to provide optimally classified voxels 1512. Here, the output (the last layer) of the fully connected layers may provide a plurality of activations for each voxel. Such a voxel activation may represent a probability measure (a prediction) defining the probability that a voxel belongs to one of a plurality of classes, e.g. dental structure classes, e.g. a tooth, jaw and/or nerve structure. For each voxel, voxel activations associated with different dental structures may e.g. be thresholded, or assigned a class by means of selecting the maximum activation per class per voxel, in order to obtain a classified voxel. Thereafter, classified voxels belonging to different dental structure classes may be represented in the image space 1523. Hence, the output of the 3D deep neural network are classified voxels in an image space that corresponds to the image space of the voxels at the input.

Figure 16:
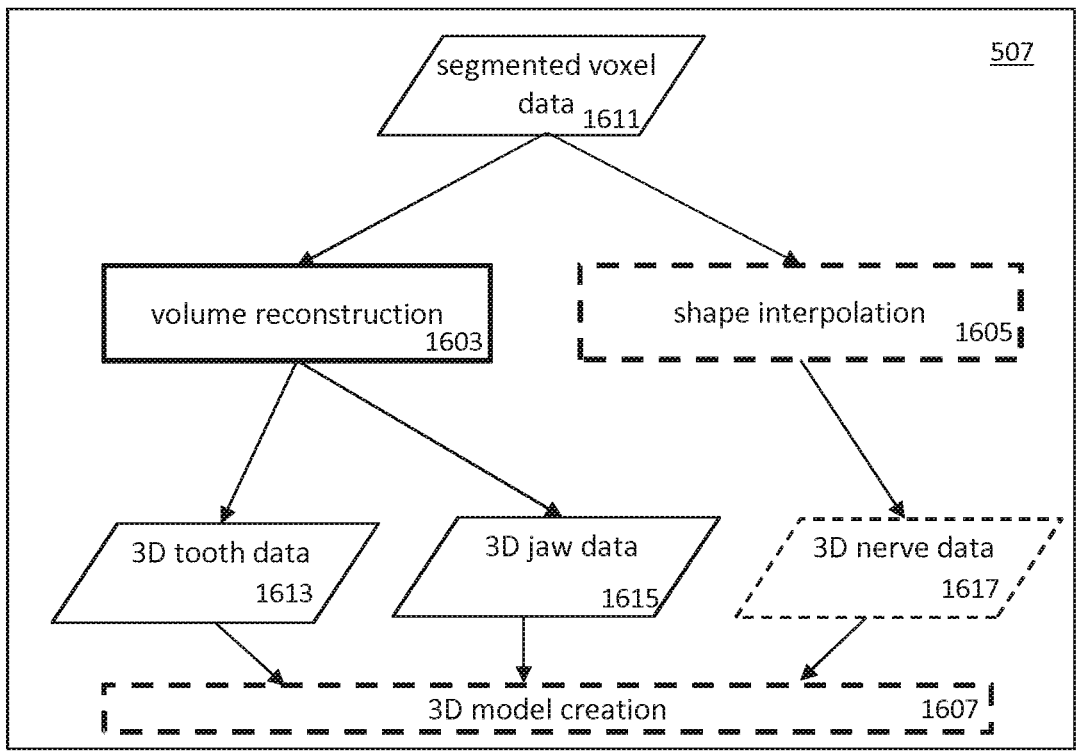
FIG. 16 shows a flow diagram of an embodiment of the segmentation processing step of FIGS. 5 and 6.

FIG. 16 shows a flow diagram of an embodiment of the segmentation processing step 507 of FIGS. 5 and 6. In steps 1603 and 1605, segmented voxel data 1611 is processed, e.g. data 545 of FIG. 5 or data 645 of FIG. 6. Segmented voxel data 1611 may comprise sets of voxels representing e.g. all those classified as belonging to a tooth, jaw or nerve structure. It may be beneficial to create 3D data of these types of structures in such a way that individual teeth and/or jaws (e.g. upper, lower) are represented by separate 3D data sets. This may be accomplished by volume reconstruction 1603. For the case of separating sets of voxels belonging to individual teeth, this may be achieved by (combinations of) 3D binary erosion, 3D marker creation and 3D watershedding.

For the combination of separation into lower and upper jaw parts, a distance from origin along the up-down (real-world coordinate system) axis may be found at which the sum of voxels in the plane perpendicular to this direction is at a minimum compared to other intersecting planes along the same axis. The split into upper and lower jaw parts can be made employing this distance. In another embodiment, the jaws may be automatically split by the deep network by classifying the corresponding voxels as separate jaw classes.

Alternatively, structures to be separated may be assigned individual classes, such as specific individual teeth, specific sections of jaw(s), etc. In such case, 1603 may consist of processing that ensures that segmented voxel data accurately and realistically represent volumes, e.g. by employing (3D) filtering techniques that ensure a consistent and realistic representation of a volume from the voxel space.

Other parts of the classified voxels, e.g. voxels that were classified by the 3D deep neural network as belonging to nerves may be post-processed by using a shape interpolation function 1605 and stored as 3D nerve data 1617. Optionally, step 1605 may be omitted if 3D nerve data 1617 is not needed. After segmentation, post-processing the 3D data of the various parts of the dento-maxillofacial structure, the nerve, jaw and tooth data 1613-1617 may be combined and formatted in separate 3D models in step 1607 that accurately represent the dento-maxillofacial structures in the 3D image data that were fed to the input of the computer system. Note that both the segmented voxel data 1611 as well as the 3D models created in step 1607 are defined in the same coordinate system as (CB)CT 3D image data 1402 of FIG. 14. Step 1607 may be skipped if 3D models are not needed, e.g. if voxel data is sufficient. The segmentation processing step 507 may additionally or alternatively output the nerve, jaw and tooth data 1613-1617.

Figure 17:
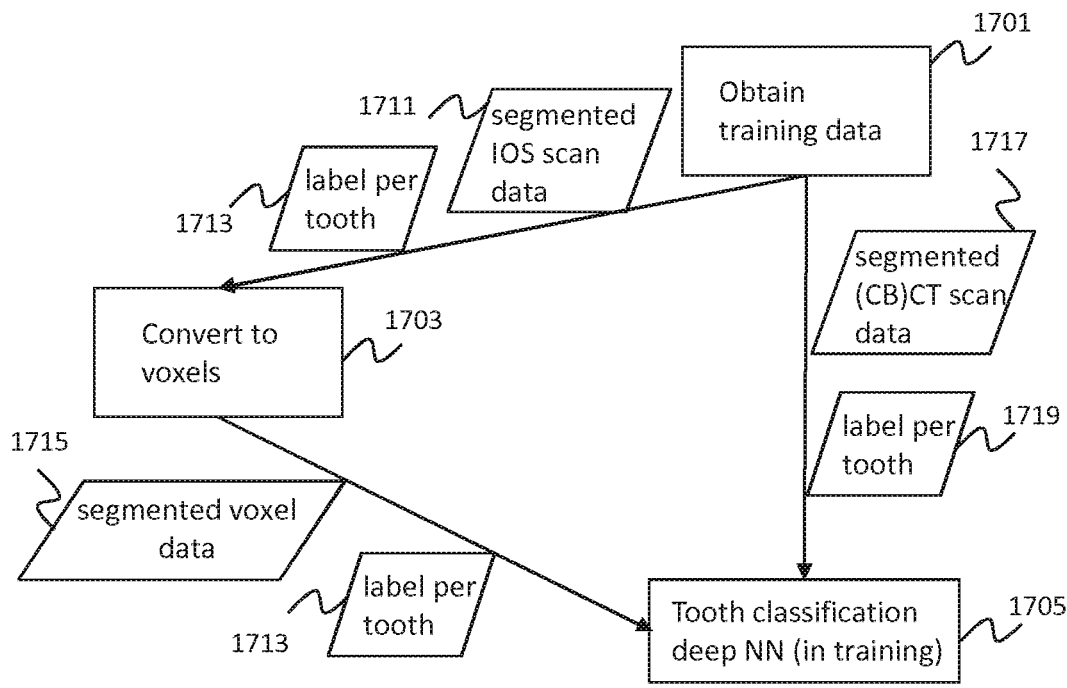
FIG. 17 shows a flow diagram of an embodiment of a method of training the classification deep neural network of FIGS. 5 and 6.

FIG. 17 shows a flow diagram of an embodiment of a method of training the classification deep neural network of FIGS. 5 and 6. Training data for the tooth classification deep neural network 1705 is obtained in step 1701. The training data may include segmented voxel data 1717 derived from a (CB)CT scan along with a label per tooth 1719 and/or segmented mesh data 1711 derived from an IOS scan (e.g. individual teeth crowns segmented from a 3D surface mesh comprising teeth and gingiva) along with a label per tooth 1713. The segmented mesh data 1711 is converted to segmented voxel data 1715 in step 1703 and then provided to the tooth classification deep neural network 1705.

The outputs of the tooth classification deep neural network are fed into classification post-processing step 511 of FIGS. 5 and 6, which is designed to make use of knowledge considering dentitions (e.g. the fact that each individual tooth index can only appear once in a single dentition) to ensure the accuracy of the classification across the set of labels applied to the teeth of the dentition. In an embodiment, correct labels may be fed back into the training data with the purpose of increasing future accuracy after additional training of the 3D deep neural network.

Methods and systems for automatic taxonomy based on deep learning are described in European patent application no. 17194460.6 and PCT application no. PCT/EP2018/076871 with title Automated classification and taxonomy of 3D teeth data using deep learning methods, which is hereby incorporated by reference in this application.

Figure 18:
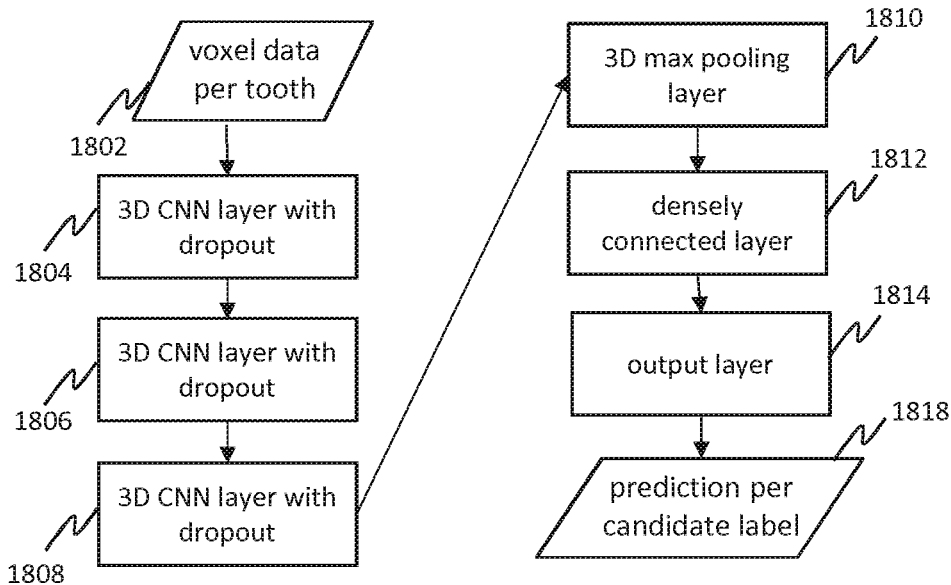
FIG. 18 depicts an example of a 3D deep neural network architecture for the classification deep neural network of FIGS. 5 and 6.

FIG. 18 depicts an example of a 3D deep neural network architecture for the classification deep neural network of FIGS. 5 and 6. The network may be implemented using 3D convolutional layers (3D CNNs). The convolutions may use an activation function. A plurality of 3D convolutional layers, 1804-1808, may be used wherein minor variations in the number of layers and their defining parameters, e.g. differing activation functions, kernel amounts, use of sub-sampling and sizes, and additional functional layers such as dropout and/or batch normalization layers may be used in the implementation without losing the essence of the design of the 3D deep neural network.

In part to reduce the dimensionality of the internal representation of the data within the 3D deep neural network, a 3D max pooling layer 1810 may be employed. At this point in the network, the internal representation may be passed to a densely-connected layer 1812 aimed at being an intermediate for translating the representation in the 3D space to activations of potential labels, in particular tooth-type labels.

The final or output layer 1814 may have the same dimensionality as the desired number of encoded labels and may be used to determine an activation value (analogous to a prediction) per potential label 1818.

The network may be trained making use of a dataset with as input for the 3D CNN layers a 3D voxel data set per tooth 1802. For each training sample (being a 3D representation of a single tooth), the corresponding correct label (labels 1713 and 1719 of FIG. 17) may be used to determine a loss between desired and actual output. This loss may be used during training as a measure to adjust parameters within the layers of the 3D deep neural network. Optimizer functions may be used during training to aid in the efficiency of the training effort. The network may be trained for any number of iterations until the internal parameters lead to a desired accuracy of results. When appropriately trained, an unlabeled sample may be presented as input and the 3D deep neural network may be used to derive a prediction for each potential label.

Hence, as the 3D deep neural network is trained to classify a 3D data sample of a tooth into one of a plurality of tooth types, e.g. 32 tooth types in case of a healthy dentition of an adult, the output of the neural network will be activation values and associated potential tooth type labels. The potential tooth type label with the highest activation value may indicate to the classification system that it is most likely that the 3D data sample of a tooth represents a tooth of the type as indicated by the label. The potential tooth type label with the lowest or a relatively low activation value may indicate to the taxonomy system that it is least likely that the 3D data set of a tooth represents a tooth of the type as indicated by such a label.

Note that it may be required to train separate specific network models (same architectures having different final parameters after specific training) based on the type of input volume, e.g. the input voxel representation being a complete tooth volume, or the input voxel representation only representing a tooth crown.

Figure 19:
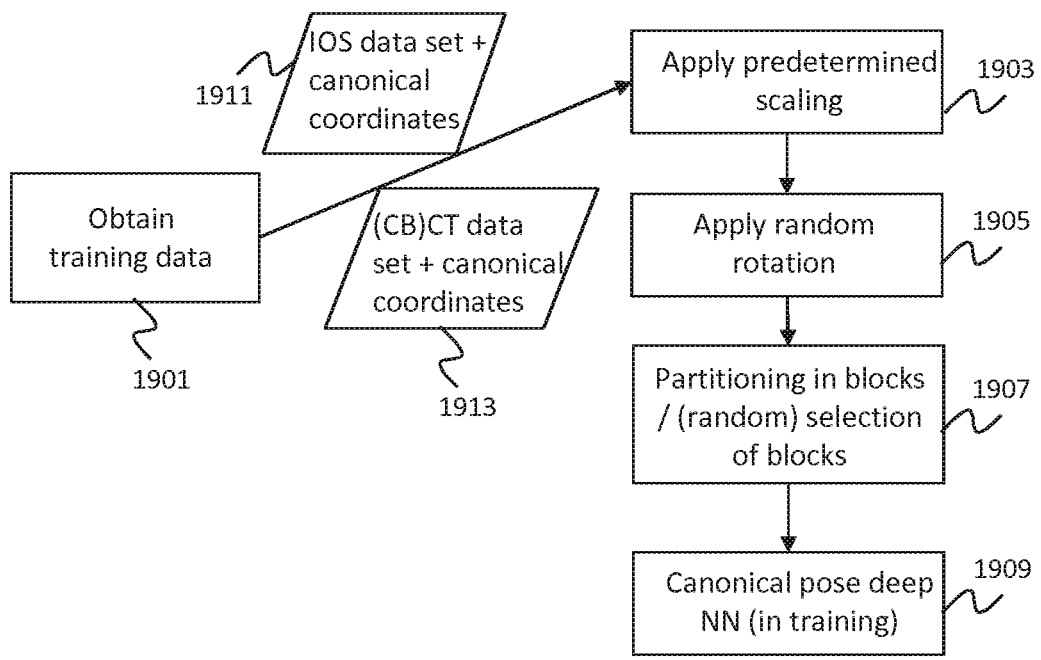
FIG. 19 shows a flow diagram of an embodiment of a method of training a canonical pose deep neural network.

FIG. 19 shows a flow diagram of an embodiment of a method of training a canonical pose deep neural network. Methods and systems for automated determination of a canonical pose of a 3D dental structure and superimposition of 3D dental structures using deep learning are also described in European patent application no. 18181421.1 and PCT application no. PCT/EP2019/067905, which is hereby incorporated by reference in this application. The network may be trained on the basis of data including 3D image samples and associated canonical coordinates. The training data may comprise 3D data sets (e.g. voxel intensity values, e.g. radio densities in the case of (CB)CT data, or binary values, e.g. in the case of voxelized surface scan data). Canonical coordinate data, which may be represented as an (x,y,z) vector per input voxel, may be used as target data. In the embodiment of FIG. 19, data sets are obtained from both IOS scans and (CB)CT scans, resulting in a first data set 1911 and a second data set 1913, respectively. Both data sets 1911 and 1913 are voxel representations. Data set 1913 may have been obtained by converting a surface mesh representation into a voxel representation.

A canonical coordinate system may be selected that is suitable for 3D dental structures. In an embodiment, in the case of a 3D dental structure, a canonical coordinate system may be determined to have an origin (0,0,0) at a consistent point (inter- and intra-patient). Henceforth, when referring to 'real-world coordinates', this is considered as having axes directions related to the patient perspective, with e.g. a patient standing upright, with lowest-highest' meaning patient perspective 'up-down', 'front-back' meaning 'front-back' from the patient perspective, and left-right' meaning patient perspective 'left-right'. 'Real world' is intended to refer to the situation from which information, such as 3D data sets, is sourced.

Such consistent point may e.g. be the lowest point (in real-world coordinates)—where both most frontally positioned teeth (FDI system index 11 and 21) are still in contact, or would be in contact (if e.g. either of those teeth is missing). Considering the directions of the axes, real-world directions (viewed as patient) down-up, left-right and front-back may respectively be defined and encoded as x, y and z-values ranging from a low value to a high value. In order to scale to real-world dimensions, various representation (meaning a specific conversion from input data to training data) methods may be employed as long as this is done consistently across all training data, as the same scaling will be the output of the 3D deep neural network. For example, a value of 1 coordinate unit per real-world distance of 1 mm may be employed.

In order to achieve a 3D deep neural network that is robust against variances in data and or data modalities, a large variety of training samples may be generated on the basis of the initial training data obtained in step 1901. To that end, step 1903 comprises downscaling a 3D data set to a downscaled 3D data set and associated canonical coordinates of a predetermined resolution. Such downscaling operation results in a smaller 3D image data set, e.g. downscaling the voxel resolution in each direction to 1 mm. Furthermore, in step 1905, different variations of one 3D data set are generated by applying random rotations to the (downscaled) 3D data and associated canonical coordinates. Note that this may be done for any available patient, effectively supplying a pool of data from which to draw potential training samples, having a multitude of patient data sets and a multitude of rotations (and/or scaling factors) per data set.

Furthermore, a step 1907 comprises partitioning the (downscaled) 3D data sets and associated canonical coordinates in blocks (3D image samples), wherein each block has a predetermined size and is a subset of the total volume of the 3D data set. For example, a 3D data set provided to the input of the training module may include a volume of 400×400×400 voxels wherein each voxel has a dimension of 0.2 mm in every orthogonal direction. This 3D data set may be downscaled to a downscaled 3D data set having a volume of e.g. 80×80×80 voxels of 1 mm in every direction. Then, the downscaled 3D data set may be divided into 3D data blocks of a predetermined size (e.g. 24×24×24 voxels of 1 mm in every direction). These blocks may be used to train the canonical pose deep neural network 1909 using the canonical coordinates as target. Step 1907 further comprises randomly selecting blocks to be provided to the canonical pose deep neural network 1909.

Note that canonical pose deep neural network 1909 will inherently train on both varying rotations (generated in step 1905) and translations (generated in step 1907) and that samples of a multitude (variety) of scales may be generated in step 1903.

Figure 20:
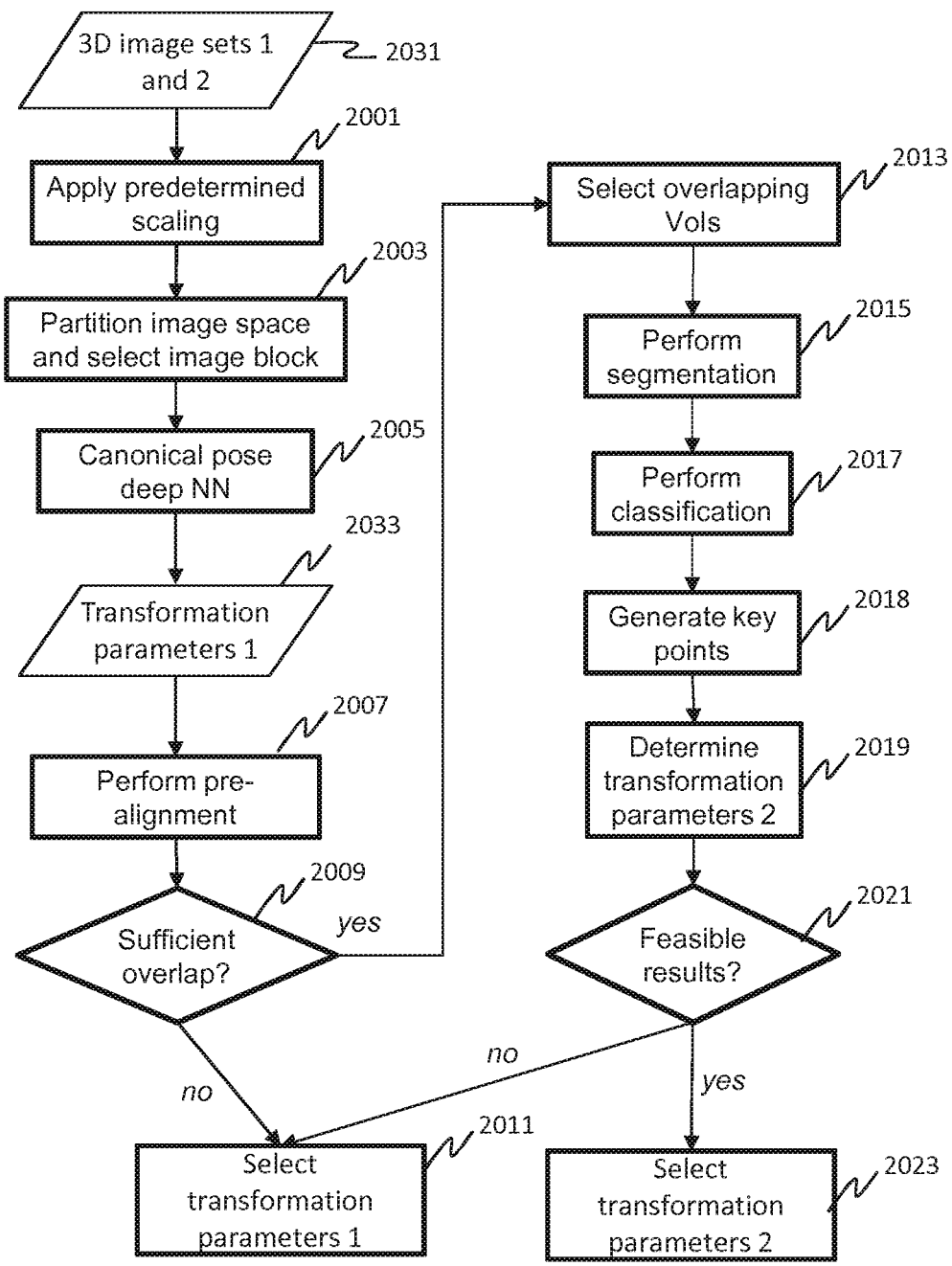
FIG. 20 shows a flow diagram of an embodiment of the alignment step of FIGS. 5 and 6.

FIG. 20 shows a flow diagram of an embodiment of the alignment step of FIGS. 5 and 6. The two input 3D image data sets 2031 shown in FIG. 20 have already been appropriately voxelized. Similarly as described in relation to FIG. 19, the two input 3D image date sets 2031 are processed employing predetermined scaling in step 2001, partitioning the down-scaled data set into image blocks of a predetermined size in step 2003, and providing the 3D image blocks to the canonical pose deep neural network 2005. By providing image blocks covering the entire space of the received 3D image data at least once, canonical coordinates can be predicted by the canonical pose deep neural network for every (down-sampled) voxel in the 3D image data set.

The canonical pose deep neural network 2005 provides a first set of transformation parameters 2033. Note that with enough training samples from a relatively large real-world 3D space, a canonical pose may be determined for received data from a smaller volume (provided it is representatively comprised within the training data). Predictions by canonical pose deep neural network 2006 may be yielded in floating point values.

Using this first set of transformation parameters 2033, pre-alignment may be performed in step 2007 and determination of sufficient overlap may be performed in step 2009. If the amount of overlap is insufficient, as according to a threshold or thresholds as may be determined experimentally and subsequently may be programmatically checked, the first set of transformation parameters may be selected in step 2011. If there is insufficient overlap, determining a second set of transformation parameters would not lead to improved results.

Following determination of sufficient overlap, a step 2013 may be performed. Step 2013 comprises selecting overlapping DOIs. Segmentation step 2015 may be performed automatically on both received 3D image data sets, either employing 3D deep neural network based methods as described above, or other methods known in the art as may be the case with IOS data. Note that in the case of the latter, such segmentations of tooth crowns may be performed on the received 3D image data in the form of surface mesh data.

Classification may be performed in step 2017 on the (segmented) structure data and the resulting information may be relayed to keypoint generation step 2018. The ability of including the identification of same teeth in the differing received data sets is expected to yield more robustness against potential variances in the amount of overlap and data quality of the received data sets.

The generated clouds of selected (sparse, closely matching) keypoints may be employed at step 2018 to determine a second set of transformation parameters for alignment. Note that any preceding transformation potentially following from 2007, 2013 may be taken into account in step 2019 to determine the first set of transformation parameters.

A sanity check may be performed in step 2021, e.g. by checking deviations the first set of transformation parameters 2033. In case of large discrepancies, the first set of transformation parameters may be selected in step 2011. Otherwise, the second set of transformation parameters may be selected in step 2023. In an alternative embodiment, both sets of transformations may be combined using weighted averages and a weight of 0 might be used for the second set of transformation parameters in case of large discrepancies. Non-feasible results may be the result of inaccurate data received, such as e.g. artefacts present in CBCT data, incorrect surface representation from IOS data, amongst others.

Point data for surfaces meshes is saved with floating point precisions, yielding potentially highly accurate results. The transformation parameters to be selected at step 2023 thus have the potential of being a highly accurate refinement upon the parameters to be selected at step 2011. The embodiment of FIG. 20 may be considered significantly more robust than current methods in the art due to the inclusion of determination of pre-alignment, overlap and segmentation and taxonomy of individual structures.

Transformation parameters may be internally represented in a variety of ways, e.g. 3 vectors of 3 values describing respectively rotations in order, 3 translation values to an origin, and/or 3 values determining applicable scaling, all having positive and/or negative magnitudes of value belonging to a specific axis in an orthogonal 3D coordinate system. Alternatively, any combination of matrices as known in linear algebra may be employed, more specifically either rotation, transformation, scaling and/or combinations as may be determined in a (affine) transformation matrix.

Prior knowledge considering accuracies, robustness, etc. may be employed to e.g. determine a weighting of importance of the two sets of transformation parameters received. The parameters may thus be programmatically combined to yield the most accurate desired transformation parameters for alignment. Note that transformation parameters may, depending on desired results, either be parameters matching set 2 to set 1, set 1 to set 2, and/or both being aligned in an alternative (desired) coordinate system.

Figure 21:
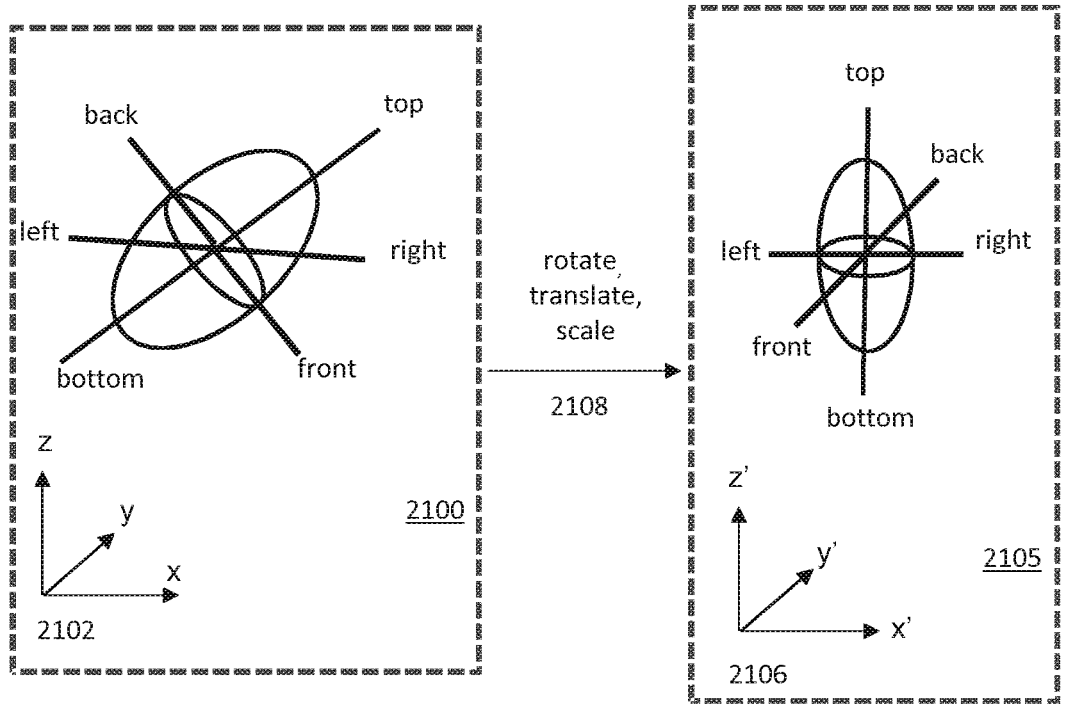
FIG. 21-23 depict schematics illustrating the execution of the method of FIG. 20.
Figure 22:
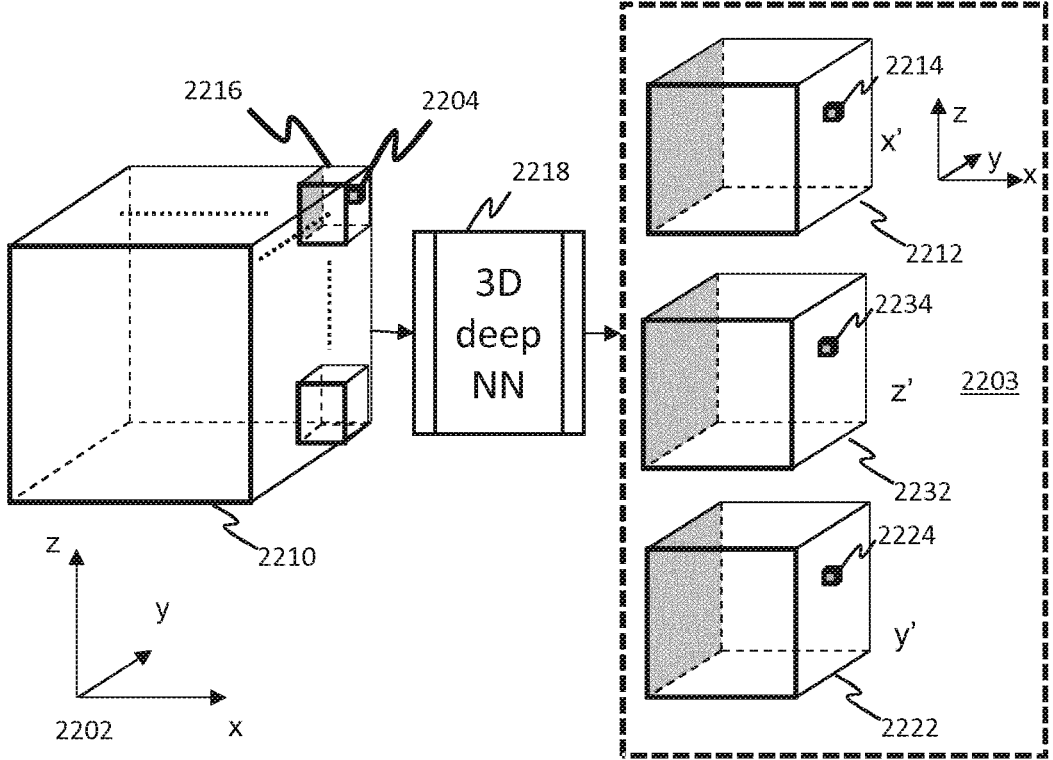
Figure 23:
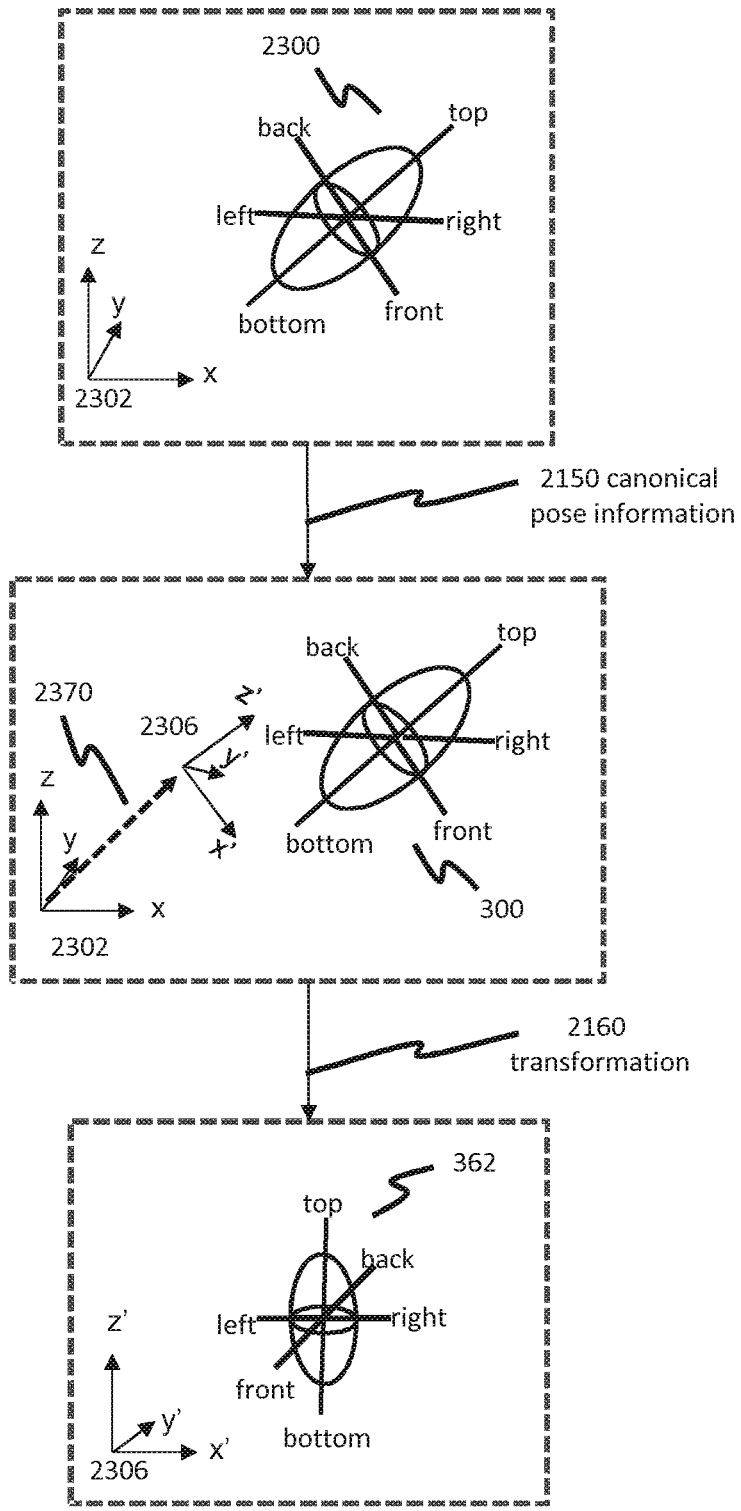

FIGS. 21-23 depict schematics illustrating the execution of the method of FIG. 20. FIG. 21 schematically depicts a voxel representation 2100 of a 3D object, e.g.

a dental object such as a tooth. A voxel may be associated with an intensity value, e.g. a radio density obtained from a (CB)CT scan. Alternatively, a voxel may be associated with a binary value. In that case, a voxel representation may be a binary voxel representation of a voxelized surface or a voxelized surface-derived volume obtained from a structured light scan or laser surface scan. The 3D object may have specific features identifying a top part (e.g. a crown), a bottom part (e.g. a root), a front part, a back part and a left and right part.

The voxel representation is associated with a first (orthogonal) coordinate system (x,y,z) 2102, e.g. a coordinate system that is used by the scanning software to represent the scanned data in a 3D space. These coordinates may e.g. be provided as (meta-)data in a DICOM image-file. The 3D object may have a certain orientation, position and size in the 3D space defined by the first coordinate system. Note however that such coordinate system may not yet correspond to a system as may be defined relative to the object, illustrated here by 'left', 'right', 'front', 'back', 'bottom' and 'top'.

Using a trained 3D deep neural network, the 3D object may be (spatially) 'normalized' (i.e. re-oriented, re-positioned and scaled) 2108 and defined based on an (orthogonal) canonical coordinate system. In the canonical coordinate system (x',y',z') 2106, the normalized 3D object 2105 may have a canonical pose, in which specific features of the 3D object may be aligned with the axis of the canonical coordinate system. Hence, the system may receive a voxel representation of a 3D dental structure having a certain orientation, position and size in a 3D space defined by a coordinate system defined by the scanning system and determine a canonical voxel representation of the 3D object wherein the 3D object is defined in a canonical coordinate system wherein the size of the objected is scaled and wherein specific features of the 3D dental structure are aligned with axes of the canonical coordinate system.

FIG. 22 depicts a 3D deep neural network 2218 which may be trained to receive voxels of a voxel representation 2210 of a 3D object, wherein voxels may have a certain position defined by a coordinate system 2202 (x,y,z). The 3D deep neural network may be configured to generate so-called canonical pose information 2203 associated with the voxel representation. The canonical pose information may comprise for each voxel 2204 (x,y,z) of the voxel representation, a prediction of a coordinate (x',y',z') in a space defined by the canonical coordinate system. The canonical coordinate system may be defined with respect to a typical position, orientation and scale of reliably identifiable dento-maxillofacial structures, e.g.

features of the dental arch. The information required to derive such canonical coordinate system may be encoded in the 3D deep neural network during the training phase of the network. This way, the canonical pose information may be used to place different varieties and/or modalities of 3D data representing the same dento-maxillofacial structure in the same relative position, orientation, and scale.

Hence, for each input voxel 2204 three corresponding output values 2214, 2224, 2234 are generated by the 3D deep neural network, comprising predictions for the values of, respectively, the input voxel's x'-, y'-, and z'-coordinates in the canonical coordinate system. In an embodiment, the canonical pose information may include three 3D voxel maps 2212, 2222, 2232 wherein each 3D voxel map links a voxel of a voxel representation at the input of the 3D neural network to a canonical coordinate.

Before providing the voxel representation to the input of the 3D deep neural network, the voxel representation may be partitioned into a set of voxel blocks (illustrated here by 2216, hereafter in short 'blocks'), wherein the dimensions of a voxel block match the dimensions of the input space of the 3D deep neural network. The block size may depend on data storage capabilities of the 3D deep neural network. Thus, the 3D deep neural network may process the voxels in each of the blocks of the voxel representation and produce canonical pose information for voxels of each block, i.e. predictions of coordinates (x',y',z') of a canonical coordinate system for each voxel in a block. In an embodiment, the 3D deep neural network may generate three voxel maps 2212, 2222, 2232, a first voxel map 2212 comprising for each voxel in a block that is offered to the input of the 3D deep neural network, a corresponding x' coordinate; a second voxel map 2222 comprising for each voxel in a block an y' coordinate; and, a third voxel map 2232 comprising for each voxel in a block an z' coordinate.

FIG. 23 schematically shows a voxel representation of a 3D object 2300 that is offered to the input of the 3D deep neural network, and defined on the basis of a first coordinate system (x,y,z) 2302, e.g. a coordinate system used by the image processing software of the scanner that was used to produce the 3D images. These coordinates or the information to determine these coordinates may be included in the data file, e.g. a DICOM file, as metadata. Based on canonical pose information generated by the 3D deep neural network a prediction of the canonical pose of the 3D object in a canonical coordinate system may be generated. Hence, the canonical pose information 2350 may link a position (x,y,z) of each voxel in the first coordinate system to a position (x',y',z') in the canonical coordinate system. This information may be used to determine a transformation 2360 that allows the system to transform the 3D object defined in the first coordinate system into its canonical pose 2362 defined in the canonical coordinate system.

The pose information may be used to determine an orientation and a scaling factor associated with the axis of the canonical coordinate system (the canonical axes). Here, the orientation may be an orientation of the canonical axes in the space defined by the first coordinate system. The pose information may also be used to determine the position of the origin of the canonical coordinate system.

An orientation of a canonical axis may be determined based on a (local) gradient in one or more voxels in a 3D voxel map as determined by the 3D deep neural network. For example, for each or at least a number of voxels of the first 3D voxel map associated with the x' component of a canonical coordinate, a local gradient may be determined. The local gradient may be represented as a 3D vector in the x,y,z space defined by the first coordinate system. The direction of the vector represents a prediction of the orientation of the canonical x'-axis at the position of the voxel. Further, the length of the vector represents a prediction of a scaling factor associated with the canonical x'-axis.

In an embodiment, a prediction for the orientation and the scaling factor associated with canonical x'-axis may be determined based on x' values of the first 3D voxel map. For example, a statistically representative measure of the predictions for voxels of the first 3D voxel map, e.g. the median or average gradient, may be determined. In an embodiment, the x' values of the first 3D voxel map may be pre-processed, e.g. smoothed and/or filtered. For example, in an embodiment, a median filter may be used to remove (local) outliers. In the same way, a prediction of an orientation and a scaling factor for the canonical y'-axis may be determined based on the y' values in the second 3D voxel map and a prediction of an orientation and a scaling factor for the canonical z'-axis may be determined based on the z' values in the third 3D voxel map. The predicted orientations of the canonical x', y', z' axes may be post-processed to ensure that the axes are orthogonal or even orthonormal. Various known schemes e.g. the Gram-Schmidt process, may be used to achieve this. Rotation and scaling parameters may be obtained by comparing the received coordinate system 2302 and the coordinate system as derived from predictions.

The position of the origin of the canonical coordinate system (in terms of a translation vector in the space of the first coordinate system) may be obtained by determining a prediction of the canonical coordinates of the center of a voxel representation that is offered to the input of the 3D deep neural network. These coordinates may be determined based on e.g. the average or median value of predicted x' values of the first 3D voxel map, y' values of the second 3D voxel map and z' values of the third 3D voxel map. A translation vector may be determined based on the predicted canonical coordinates (xo',yo',zo') of the center of the block and the coordinates of the center of the blocks based on the first coordinate system, e.g. using a simple subtraction. Alternatively, the origin of the canonical coordinate system may be determined by an aggregation of multiple predictions of such blocks, the latter effectively processing canonical coordinates as determined for the space of the same size of the received voxel representation. The above described process may be repeated for each or at least a large part of the blocks of a 3D data set. The information determined for each block (orientation, scale and origin of the canonical coordinate system) may be used to obtain e.g. averaged values over multiple blocks, providing an accurate prediction.

Figure 24:
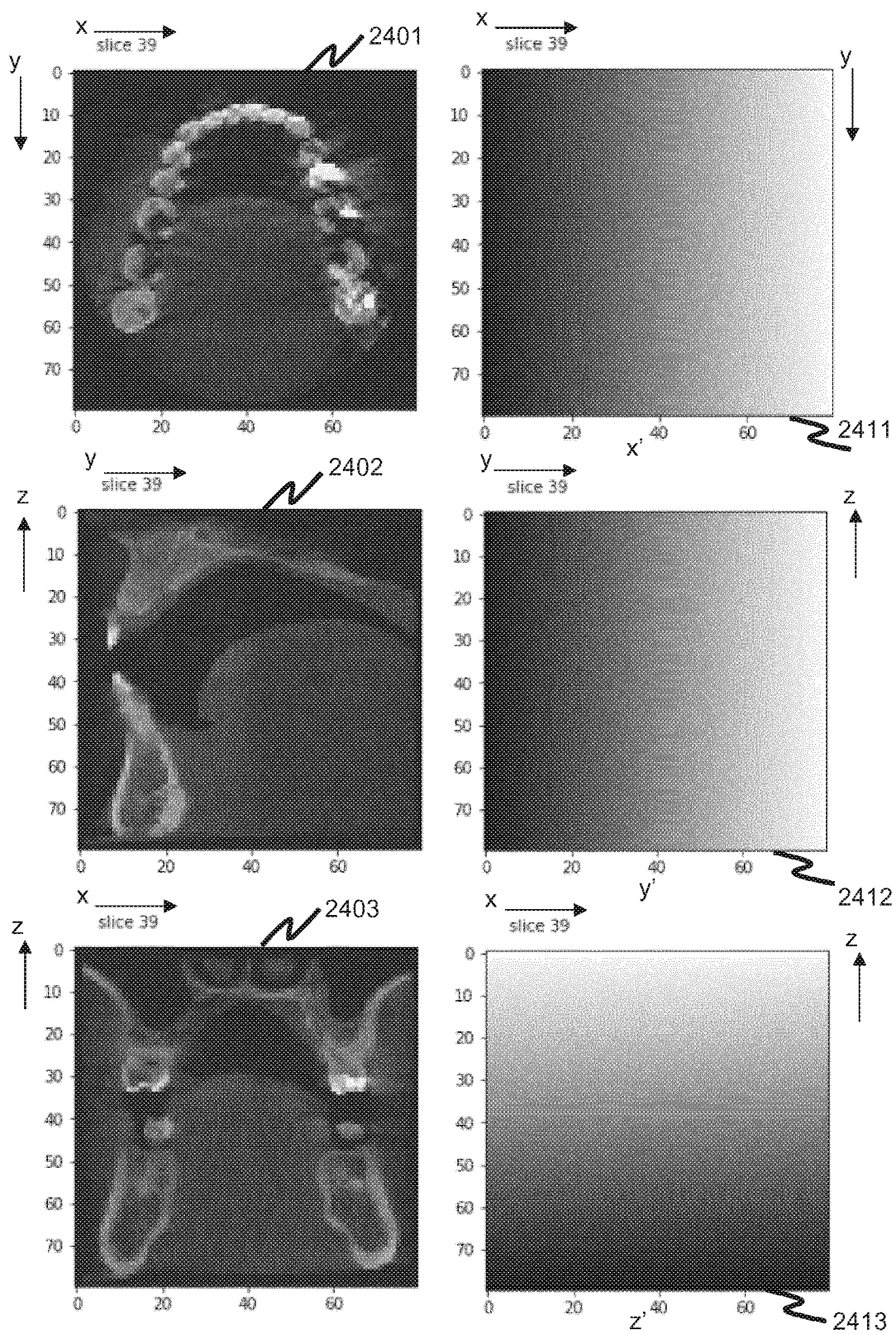
FIG. 24 illustrates training and prediction data employed by the method of FIG. 20.

FIG. 24 illustrates training data employed by the method of FIG. 20. FIG. 24 depicts three slices 2401-2403 of a 3D data set, in this example a CBCT scan of a 3D dental structure, and associated slices of the 3D voxel maps for the x', y' and z' coordinate as may be used to train a 3D deep neural network. These 3D voxel maps comprise the desired predictions of the canonical x' coordinate 2411, the canonical y' coordinate 2412 and the canonical z' coordinate 2413. The grayscale values visualize the gradients of (encoded) values for coordinates according to the canonical coordinate system. The coordinates (x, y, z) indicate the position of a voxel of the 3D dental structure based on a coordinate system associated with the CBCT scan. The axes as visualized including their directions are denoted top-left and top-right per picture. Note that all visualizations are 2D representations of a single middle 'slice' (effectively pixels of 2D image data), as sliced from the actually employed 3D data set and the associated voxel maps, as denoted by the slice number visible top-left per illustration.

Figure 25:
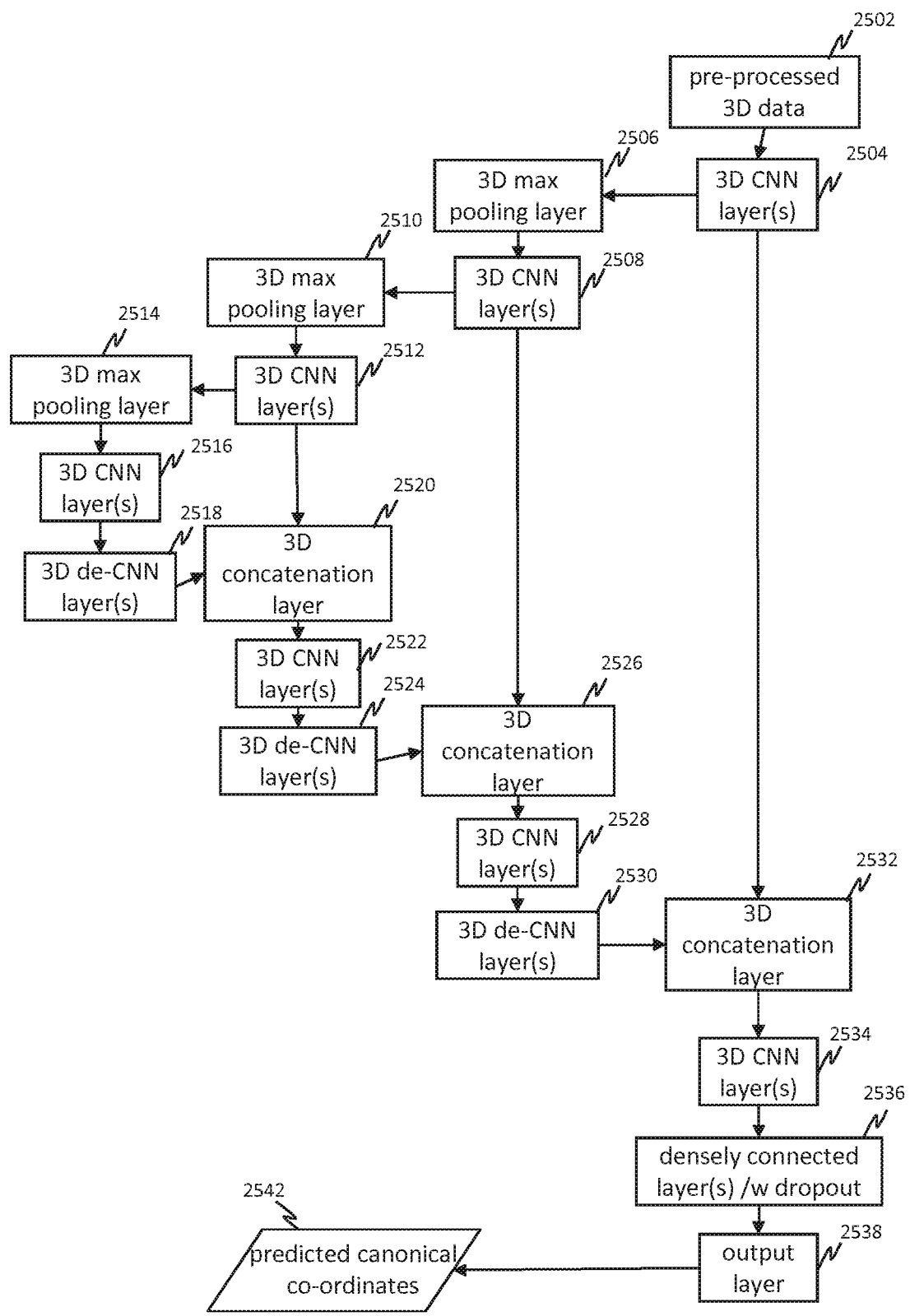
FIG. 25 depicts an example of a 3D deep neural network architecture for the canonical pose deep neural network of FIG. 20.

FIG. 25 depicts an example of a 3D deep neural network architecture for the canonical pose deep neural network of FIG. 20. The 3D deep neural network may have an architecture similar to a 3D U-net, which is effectively a 3D implementation of the 2D U-net as is known in the art.

The network may be implemented using a variety of 3D neural network layers, such as (dilated) convolutional layers (3D CNNs), 3D max-pooling layers, 3D deconvolutional layers (3D de-CNNs), and densely connected layers. The layers may use a variety of activation functions such as linear, tanh, ReLU, PreLU, sigmoid, etc. The 3D CNN and de-CNN layers may vary in their amount of filters, filter sizes and subsampling parameters. The 3D CNN and de-CNN layers, as well as the densely connected layers, may vary in their parameter initialization methods. Dropout layers and/or batch normalization may be employed throughout the architecture.

As with a 3D U-net architecture, during training the various filters within the 3D CNN and 3D de-CNN layers learn to encode meaningful features as would aid the effort of prediction accuracy. During training, matching sets of 3D image data and encoded matching canonical coordinates are used to optimize towards prediction of the latter from the former. A loss function may be employed as a measure to be minimized. This optimization effort may be aided by making use of optimizers such as SGD, Adam, etc.

Such an architecture may employ various resolution scales, effectively downscaling 2506, 2510, 2514 as results from a previous set of 3D CNN layers 2504, 2508, 2512 through max pooling or (dilated and/or subsampling) convolutional layers. The term 'meaningful features' refers to (successive) derivations of information relevant to determining the target output values, and are also encoded through the 3D de-CNN layers, which effectively perform an upscaling whilst employing filters. By combining 2520, 2526, 2532 data resulting from such 3D de-CNN layers 2518, 2524, 2534 with the data from the 'last' 3D CNN layers operating on the same resolution (2512 to 2520, 2508 to 2526 and 2504 to 2532), highly accurate predictions may be achieved. Throughout the upscaling section of the architecture (starting at 2518), additional 3D CNN layers may be used 2522, 2528, 2534. Additional logic may be encoded within the parameters of the network by making use of densely connected layers distilling e.g. logic per voxel based on the results of the filters of the incoming 3D CNN layer 2534.

When being utilized for inference, having been trained to have encoded internal parameters in such a way that validation yields sufficiently accurate results, an input sample may be presented and the 3D deep neural network may yield predicted canonical coordinates per voxel 2542.

Figure 26:
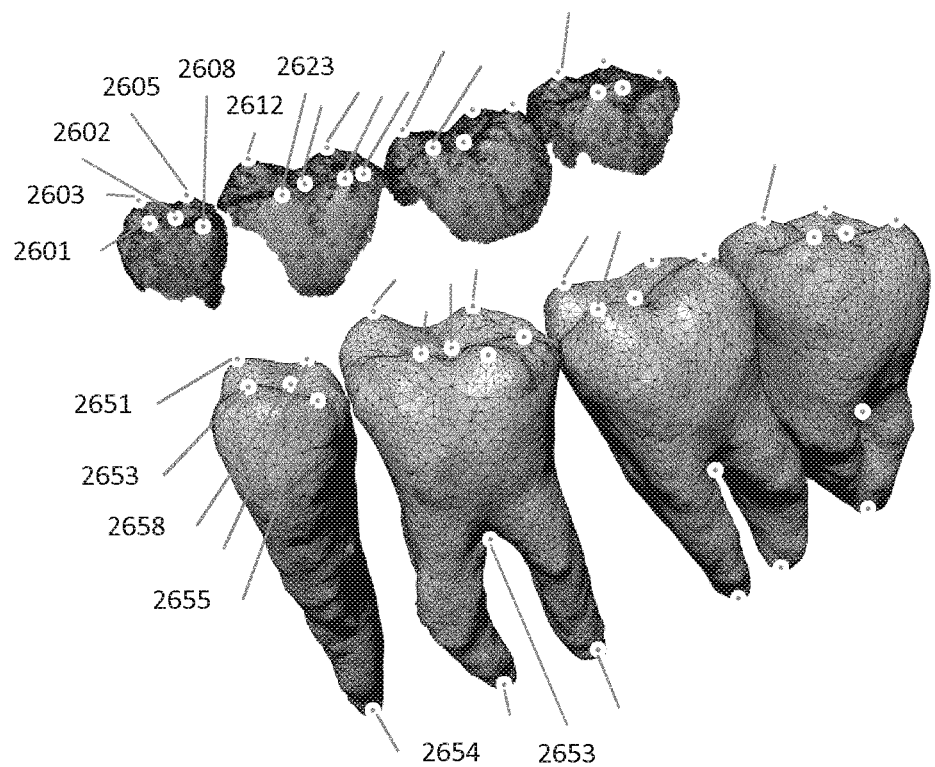
FIG. 26 illustrates an example of key points generated by the method of FIG. 20.

FIG. 26 illustrates an example of key points generated by the method of FIG. 20. The keypoints are generated, for example, from the surface meshes (3D models) created in step 1607 of FIG. 16 and characterize these surfaces. In effect, this may be considered as a reduction step to reduce all available points within a surface mesh to a set of most relevant (most salient) points. This reduction is beneficial since it reduces processing time and memory requirements. In addition, methods for determination of such points may be selected that are expected to yield roughly the same set of points even if the inputs for the generation are slightly divergent (sets of) 3D surface meshes (still representing the same structures).

Well known methods in the art for determining keypoints from surface meshes usually include the determination of local or global surface descriptors (or features) that may be hand-crafted (manually engineered) and/or machine-learned and optimized for repeatability across (slightly varying) input surface meshes, and may be optimized for performance (speed of determining the salient or keypoints), e.g. as taught by TONIONI A, et al. in "*Learning to detect good 3D keypoints*.", Int J Comput Vis. 2018 Vol .126, pages 1-20. Examples of such features are local and global minima or maxima in surface curvature.

Shown in FIG. 26 are computer renders of a 3D image data set, including the edges and vertices defining the meshes of surface faces and hence showing the points defining the surfaces. The top four objects are individually processed and segmented tooth crowns derived from an intra-oral scan. The bottom four objects are individual teeth derived from a CBCT scan with the afore-mentioned segmentation deep neural network. These two sets of four teeth are sourced from the same patient at approximately the same moment in time. They have been roughly pre-aligned using transformation parameters output by the afore-mentioned canonical pose neural network. From these pre-aligned data sets, overlapping volumes were determined, and the 3D structures were segmented into separate surface meshes representing individual teeth.

In particular, in FIG. 26, points have been visualized with labels according to the format P[no. of received data set]-[no. of point]; the number of points has been reduced for visualization purposes. As can be seen, each received set of 3D image data after keypoint generation has its own set of keypoints following from salient features of the volume, where the same points along the surfaces will be marked with an (albeit arbitrarily numbered) keypoint. Note that it would be possible to sub-group such points per individual tooth within the originating 3D data set, but this would yield no additional benefits since the (same) individual tooth would not be identifiable across the different 3D data sets.

It is noteworthy that 3D surface mesh data (and point cloud data or a collection of keypoints) is in general saved in a format of orthogonal x-, y- and z-coordinates by means of floating point numbers. This opens up the potential of highly accurate determination locations of keypoints, and hence highly accurate alignment results having determined transformation parameters based on e.g. methods minimizing a computed distance between such clouds of keypoints, as may be the case when employing e.g. an iterative closest point method. Note that for determination of alignment transformation parameters, at least three non-colinear points need to be determined.

In the example of FIG. 26, keypoints are generated for the surface mesh describing the entire volume of all teeth present. It should be noted that more accurate final transformation parameters may be generated by performing e.g. keypoint generation and keypoint aligned on subvolumes, e.g. each individual tooth that is recognized across both input data sets. This data is generated, as described with reference to the previously described segmentation method. In such an alternative embodiment, a multitude of transformation parameters may be generated and from this multitude, outliers may be removed and the set of parameters may be averaged into a single set of parameters for the purpose of alignment of the input data sets.

Figure 27:
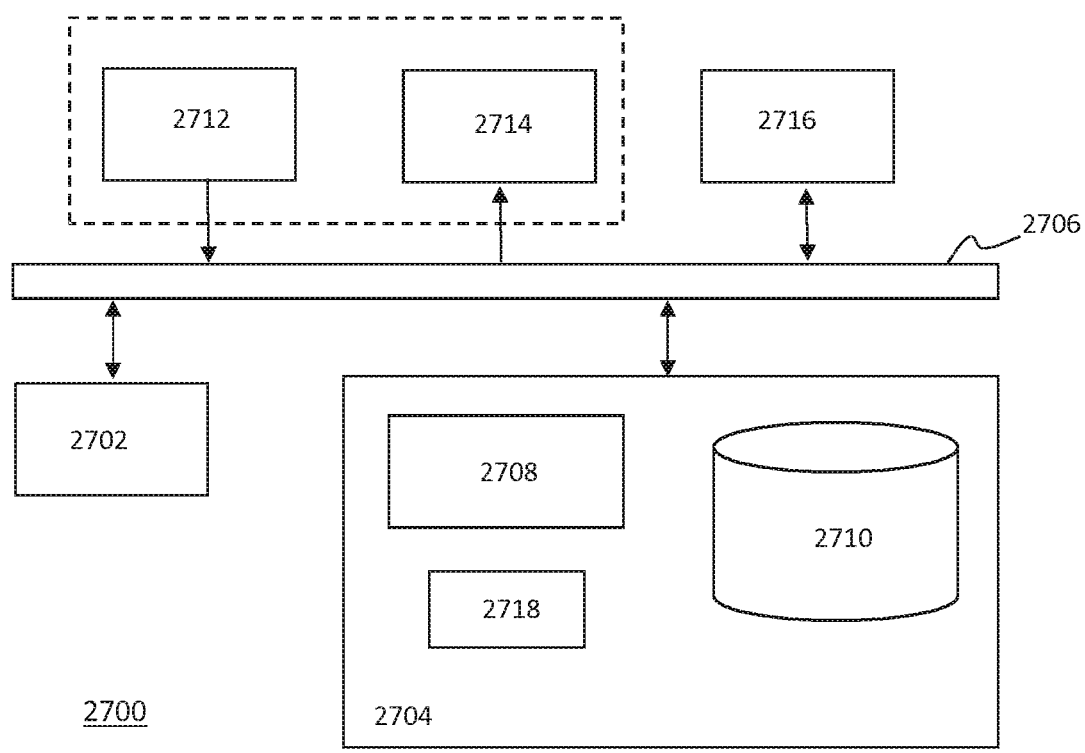
FIG. 27 is a block diagram of an exemplary data processing system for performing the methods of the invention.

FIG. 27 depicts a block diagram illustrating an exemplary data processing system that may perform the method as described with reference to FIGS. 1-2, 5-8, 10-11,13, 16-17, and 19-20.

As shown in FIG. 27, the data processing system 2700 may include at least one processor 2702 coupled to memory elements 2704 through a system bus 2706.

As such, the data processing system may store program code within memory elements 2704. Further, the processor 2702 may execute the program code accessed from the memory elements 2704 via a system bus 2706. In one aspect, the data processing system may be implemented as a computer that is suitable for storing and/or executing program code. It should be appreciated, however, that the data processing system 2700 may be implemented in the form of any system including a processor and a memory that is capable of performing the functions described within this specification.

The memory elements 2704 may include one or more physical memory devices such as, for example, local memory 2708 and one or more bulk storage devices 2710. The local memory may refer to random access memory or other non-persistent memory device(s) generally used during actual execution of the program code. A bulk storage device may be implemented as a hard drive or other persistent data storage device. The processing system 2700 may also include one or more cache memories (not shown) that provide temporary storage of at least some program code in order to reduce the number of times program code must be retrieved from the bulk storage device 2710 during execution.

Input/output (I/O) devices depicted as an input device 2712 and an output device 2714 optionally can be coupled to the data processing system. Examples of input devices may include, but are not limited to, a keyboard, a pointing device such as a mouse, or the like. Examples of output devices may include, but are not limited to, a monitor or a display, speakers, or the like. Input and/or output devices may be coupled to the data processing system either directly or through intervening I/O controllers.

In an embodiment, the input and the output devices may be implemented as a combined input/output device (illustrated in FIG. 27 with a dashed line surrounding the input device 2712 and the output device 2714). An example of such a combined device is a touch sensitive display, also sometimes referred to as a "touch screen display" or simply "touch screen". In such an embodiment, input to the device may be provided by a movement of a physical object, such as e.g. a stylus or a finger of a user, on or near the touch screen display.

A network adapter 2716 may also be coupled to the data processing system to enable it to become coupled to other systems, computer systems, remote network devices, and/or remote storage devices through intervening private or public networks. The network adapter may comprise a data receiver for receiving data that is transmitted by said systems, devices and/or networks to the data processing system 2700, and a data transmitter for transmitting data from the data processing system 2700 to said systems, devices and/or networks. Modems, cable modems, and Ethernet cards are examples of different types of network adapter that may be used with the data processing system 2700.

As pictured in FIG. 27, the memory elements 2704 may store an application 2718. In various embodiments, the application 2718 may be stored in the local memory 2708, the one or more bulk storage devices 2710, or separate from the local memory and the bulk storage devices. It should be appreciated that the data processing system 2700 may further execute an operating system (not shown in FIG. 27) that can facilitate execution of the application 2718. The application 2718, being implemented in the form of executable program code, can be executed by the data processing system 2700, e.g., by the processor 2702. Responsive to executing the application, the data processing system 2700 may be configured to perform one or more operations or method steps described herein.

Various embodiments of the invention may be implemented as a program product for use with a computer system, where the program(s) of the program product define functions of the embodiments (including the methods described herein). In one embodiment, the program(s) can be contained on a variety of non-transitory computer-readable storage media, where, as used herein, the expression "non-transitory computer readable storage media" comprises all computer-readable media, with the sole exception being a transitory, propagating signal. In another embodiment, the program(s) can be contained on a variety of transitory computer-readable storage media. Illustrative computer-readable storage media include, but are not limited to: (i) non-writable storage media (e.g., read-only memory devices within a computer such as CD-ROM disks readable by a CD-ROM drive, ROM chips or any type of solid-state non-volatile semiconductor memory) on which information is permanently stored; and (ii) writable storage media (e.g., flash memory, floppy disks within a diskette drive or hard-disk drive or any type of solid-state random-access semiconductor memory) on which alterable information is stored. The computer program may be run on the processor 2702 described herein.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of embodiments of the present invention has been presented for purposes of illustration, but is not intended to be exhaustive or limited to the implementations in the form disclosed. Many modifications and variations will be apparent to those of ordinary skill in the art without departing from the scope and spirit of the present invention. The embodiments were chosen and described in order to best explain the principles and some practical applications of the present invention, and to enable others of ordinary skill in the art to understand the present invention for various embodiments with various modifications as are suited to the particular use contemplated.

Figure 28:
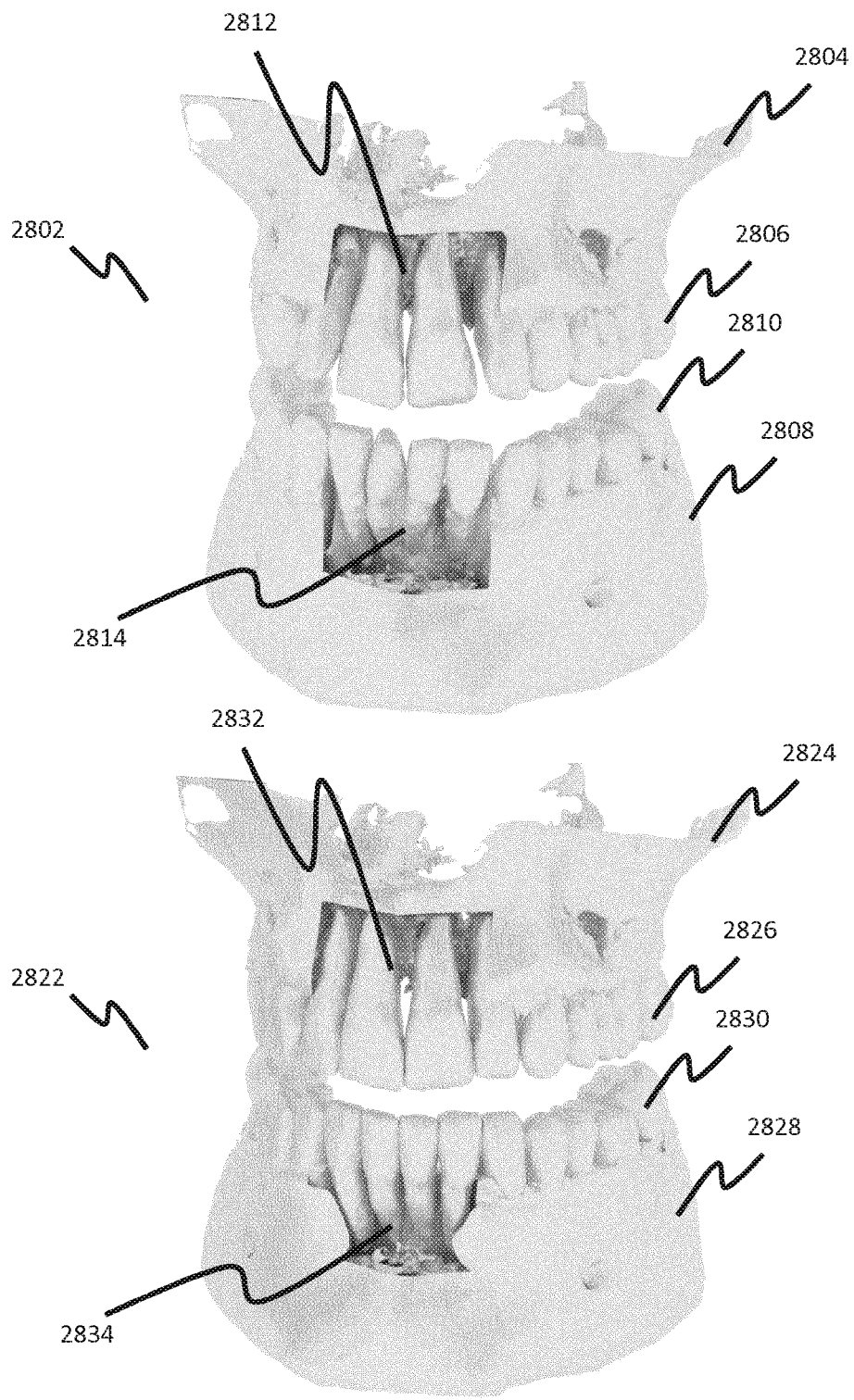
FIG. 28 shows a visualization of results of orthodontic treatment planning according to various embodiments of the invention.

FIG. 28 shows a visualization of results of orthodontic treatment planning according to various embodiments of the invention. The visualization consists of computer renders (renderings) of surface meshes as derived from internal data representations as may be encountered throughout the system(s) as described. In particular, 2802 and 2822 show visualizations of respectively before and after treatment 3D data representations. 2802 shows dental structures segmented in step 503 of FIG. 6, derived from an input CBCT scan. Separate structures are upper- and lower jaw 2804 and 2808, and the individual sets of teeth belonging to these jaws 2806 and 2810. For the purpose of this illustration, the surfaces of both jaws as indicated at 2812 and 2814 have been removed to show the relevant structural information aside from that which is directly visible, here being information considering teeth roots and intra jaw structure.

Analogous to 2802, 2822 shows, for the same patient, upper- and lower jaw 2824, 2828, the respective sets of teeth 2826, 2830 and removed jaw surfaces 2832, 2834. The individual teeth have been placed in their final desired position as may be determined by a system, as shown for example in FIG. 6. It can be seen that the teeth have been displaced in such a way that desired occlusion is achieved, no collisions are present, and no teeth (roots) have been placed outside of the appropriate local outer boundaries of the jaw. In this specific case, after incorporation of IOS data and desired attachments, the final positions as shown may be employed to e.g. produce a final aligner in a series to be used during treatment.

The invention claimed is:

1. A system comprising a deep neural network and at least one processor configured to:
   obtain a plurality of training dental computed tomography scans which reflect a moment before respective successful orthodontic treatments,
   identify individual teeth and jaw bone in each of said training dental computed tomography scans, and
   train said deep neural network with training input data obtained from said plurality of training dental computed tomography scans and training target data per training dental computed tomography scan to determine a desired final position per tooth from input data obtained from a patient dental computed tomography scan, wherein training input data obtained from each training dental computed tomography scan represents all teeth and an entire alveolar process and identifies said individual teeth and said jaw bone,
   wherein said input data comprises an image data set or a 3D data set along with information delineating said individual teeth and said jaw bone, said image data set representing an entire computed tomography scan, or multiple 3D data sets, said multiple 3D data sets comprising a 3D data set per tooth and a 3D data set for said jaw bone, and wherein
   said training target data comprises an indicator indicating an achieved transformation per tooth for one or more of said plurality of training dental computed tomography scans, said transformation comprising a translation and/or a rotation per tooth, and/or
   said training target data comprises data obtained from one or more further training dental computed tomography scans which reflect a moment after a successful orthodontic treatment, each of said one or more further training dental computed tomography scans being associated with a training dental computed tomography scan of said plurality of training dental computed tomography scans.

2. The system as claimed in claim 1, wherein said at least one processor is configured to use said identification of said individual teeth and said jaw bone to determine dento-physical properties for each of said training dental computed tomography scans and facilitate an encoding of information reflecting said dento-physical properties in said deep neural network.

3. The system as claimed in claim 2, wherein said dento-physical properties are encoded in said deep neural network by training said deep neural network with a loss function which depends on said determined dento-physical properties.

4. The system as claimed in claim 1, wherein said training data obtained from said training dental computed tomography scan further represents all basal bone.

5. The system as claimed in claim 1, wherein one or more of said plurality of training dental computed tomography scans are each associated with an indicator indicating an attachment type per tooth, said indicator being included in said training target data.

6. The system as claimed in claim 1, wherein said at least one processor is configured to obtain at least one of said one or more training dental computer tomography scans by transforming data resulting from one of said further training dental computed tomography scans.

7. The system as claimed in claim 1, wherein said at least one processor is configured to train said deep neural network with said training input data obtained from said plurality of training dental computed tomography scans and said training target data per training dental computed tomography scan to determine said desired final position and an attachment type per tooth from said input data obtained from said patient dental computed tomography scan.

8. The system as claimed in claim 1, wherein said individual teeth and said jaw bone are identified from said computer tomography scan using a further deep neural network.

9. A system comprising a deep neural network and at least one processor,
   said deep neural network being trained with training input data obtained from a plurality of training dental computed tomography scans and training target data per training dental computed tomography scan to determine a desired final position per tooth from input data obtained from a patient dental computed tomography scan,
   wherein said plurality of training dental computed tomography scans reflect a moment before respective successful orthodontic treatments, individual teeth and jaw bone are identified in each of said training dental computed tomography scans, and training input data obtained from each training dental computed tomography scan represents all teeth and an entire alveolar process and identifies said individual teeth and said jaw bone, and
   wherein said training target data comprises an indicator indicating an achieved transformation per tooth for one or more of said plurality of training dental computed tomography scans, said transformation comprising a translation and/or a rotation per tooth, and/or
   said training target data comprises data obtained from one or more further training dental computed tomography scans which reflect a moment after a successful orthodontic treatment, each of said one or more further training dental computed tomography scans being associated with a training dental computed tomography scan of said plurality of training dental computed tomography scans, and
   said at least one processor being configured to:
   obtain a patient dental computed tomography scan,
   identify individual teeth and the jaw bone in said patient dental computed tomography scan, and
   use said deep neural network to determine a desired final position per tooth from input data obtained from said patient dental computed tomography scan, wherein said input data represents all teeth and the entire alveolar process and identifies said individual teeth and said jaw bone,
   wherein said input data comprises an image data set or a 3D data set along with information delineating said individual teeth and said jaw bone, said image data set representing an entire computed tomography scan, or multiple 3D data sets, said multiple 3D data sets comprising a 3D data set per tooth and a 3D data set for said jaw bone, and wherein said determined desired final positions are used to determine a sequence of desired intermediate positions per tooth and said determined intermediate positions and said determined final positions are used to create three-dimensional representations of teeth and/or aligners.

10. The system as claimed in claim 9, wherein said at least one processor is configured to determine said sequence of desired intermediate positions per tooth based on said determined desired final positions and create said three-dimensional representations of said aligners based on said intermediate and final positions.

11. The system as claimed in claim 10, wherein said at least one processor is configured to determine three-dimensional representations of said teeth in each of said intermediate and final positions per tooth for a purpose of manufacturing aligners based on said three-dimensional representations.

12. The system as claimed in claim 11, wherein said at least one processor is configured to create said three dimensional representations of said teeth further based on data relating to tooth crowns obtained from an intraoral scan.

13. The system as claimed in claim 9, wherein said at least one processor is configured to:
use said deep neural network to determine said desired final position and an attachment type per tooth from said input data obtained from said patient dental computed tomography scan,
wherein said determined intermediate positions, said determined final positions and said attachment types are used to create said three-dimensional representations of said teeth and/or said aligners.

14. A computer-implemented method to create three-dimensional representations of teeth and/or aligners, the method comprising:
providing a deep neural network trained with training input data obtained from a plurality of training dental computed tomography scans and training target data per training dental computed tomography scan to determine a desired final position per tooth from input data obtained from a patient dental computed tomography scan, wherein said plurality of training dental computed tomography scans reflect a moment before respective successful orthodontic treatments, individual teeth and jaw bone are identified in each of said training dental computed tomography scans, and training input data obtained from each training dental computed tomography scan represents all teeth and an entire alveolar process and identifies said individual teeth and said jaw bone, and wherein said training target data comprises an indicator indicating an achieved transformation per tooth for one or more of said plurality of training dental computed tomography scans, said transformation comprising a translation and/or a rotation per tooth, and/or said training target data comprises data obtained from one or more further training dental computed tomography scans which reflect a moment after a successful orthodontic treatment, each of said one or more further training dental computed tomography scans being associated with a training dental computed tomography scan of said plurality of training dental computed tomography scans,
obtaining input data from a patient dental computed tomography scan, wherein said input data comprises an image data set or a 3D data set along with information delineating said individual teeth and said jaw bone, said image data set representing an entire computed tomography scan, or multiple 3D data sets, said multiple 3D data sets comprising a 3D data set per tooth and a 3D data set for said jaw bone,
identifying individual teeth and the jaw bone in said patient dental computed tomography scan,
using at least one processor and said deep neural network to determine a desired final position per tooth from said input data obtained from said patient dental computed tomography scan, wherein said input data represents all teeth and the entire alveolar process and identifies said individual teeth and said jaw bone,
using the at least one processor and said determined desired final positions to determine a sequence of desired intermediate positions per tooth and said determined intermediate positions, and
using the at least one processor and said determined final positions to create three-dimensional representations of teeth and/or aligners.

15. The computer-implemented method as claimed in claim 14, wherein
using the at least one processor and said deep neural network to determine said desired final position, includes determining an attachment type per tooth from said input data obtained from said patient dental computed tomography scan, and
wherein said determined intermediate positions, said determined final positions and said attachment types are used to create said three-dimensional representations of said teeth and/or said aligners.

16. A computer-implemented method comprising:
obtaining a plurality of training dental computed tomography scans which reflect a moment before respective successful orthodontic treatments,
identifying individual teeth and jaw bone in each of said training dental computed tomography scans, and
training a deep neural network using at least one processor with training input data obtained from said plurality of training dental computed tomography scans and training target data per training dental computed tomography scan to determine a desired final position per tooth from input data obtained from a patient dental computed tomography scan, wherein training input data obtained from each training dental computed tomography scan represents all teeth and an entire alveolar process and identifies said individual teeth and said jaw bone,
wherein said input data comprises an image data set or a 3D data set along with information delineating said individual teeth and said jaw bone, said image data set representing an entire computed tomography scan, or multiple 3D data sets, said multiple 3D data sets comprising a 3D data set per tooth and a 3D data set for said jaw bone, and wherein
said training target data comprises an indicator indicating an achieved transformation per tooth for one or more of said plurality of training dental computed tomography scans, said transformation comprising a translation and/or a rotation per tooth, and/or
said training target data comprises data obtained from one or more further training dental computed tomography scans which reflect a moment after a successful orthodontic treatment, each of said one or more further training dental computed tomography scans being associated with a training dental computed tomography scan of said plurality of training dental computed tomography scans.

17. The computer-implemented method as claimed in claim 16, further comprising using the at least one processor and said identification of said individual teeth and said jaw bone to determine dento-physical properties for each of said training dental computed tomography scans and facilitate an encoding of information reflecting said dento-physical properties in said deep neural network.

18. The computer-implemented method as claimed in claim 17, wherein said dento-physical properties are encoded in said deep neural network by training said deep neural network with a loss function which depends on said determined dento-physical properties.

19. The computer-implemented method as claimed in claim 16, wherein said training data obtained from said training dental computed tomography scan further represents all basal bone.

20. The computer-implemented method as claimed in claim 16, wherein one or more of said plurality of training dental computed tomography scans are each associated with an indicator indicating an attachment type per tooth, said indicator being included in said training target data.

* * * * *